(12) United States Patent
Roberts et al.

(10) Patent No.: US 7,304,085 B2
(45) Date of Patent: Dec. 4, 2007

(54) NITROGEN-CONTAINING HETEROARYL DERIVATIVES

(75) Inventors: Christopher D. Roberts, Belmont, CA (US); Dong-Fang Shi, Fremont, CA (US); Ronald C. Griffith, Escondido, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 10/861,765

(22) Filed: Jun. 4, 2004

(65) Prior Publication Data

US 2005/0154040 A1  Jul. 14, 2005

Related U.S. Application Data

(60) Provisional application No. 60/476,141, filed on Jun. 4, 2003.

(51) Int. Cl.
*A61K 31/4184* (2006.01)
*C07D 235/18* (2006.01)

(52) U.S. Cl. .................. 514/394; 548/310.7
(58) Field of Classification Search ............ 548/310.7; 514/394
See application file for complete search history.

(56) References Cited

U.S. PATENT DOCUMENTS

| 6,770,666 B2 | 8/2004 | Hashimoto et al. |
| 2004/0082635 A1 | 4/2004 | Hashimoto et al. |

FOREIGN PATENT DOCUMENTS

| CA | 2 423 800 | 3/2003 |
| WO | WO 01/90121 | 5/2001 |
| WO | WO 01/47883 | 7/2001 |
| WO | WO 02/04425 | 1/2002 |
| WO | WO 02/18404 | 3/2002 |
| WO | WO 02/057287 | 7/2002 |
| WO | WO 02/057425 | 7/2002 |
| WO | WO 03/026587 | 4/2003 |
| WO | WO 03/101993 | 12/2003 |

OTHER PUBLICATIONS

Leyssen et al., Clinical Microbiology Reviews, Jan. 2000, 13(3), pp. 67-82.*
Giangaspero, et al. "Serological and antigenical findings indicating pestivirius in man" *Arch. Virol. Suppl.*, 7:53-62 (1993).
Giangaspero, et al. "Anti-bovine viral diarrhea virus antibodies in adult Zambian patients infected with the human immunodeficiency virus" *Int. J. STD. AIDS*, 4(5):300-302 (1993).
Yolken, "Infantile Gastroenteritis Associated with Excretion of Pestivirus Antigens" et al., *Lancet*, 1(8637):517-520 (1989).
Wilks, et al. "Bovine Pestivirus and Human Infection" *Lancet*, 1(8629):107 (1989).
Giangaspero, et al. "Bovine Viral Diarrhoea" *Lancet*, 2:110 (1988).
Potts, et al. "Possible Role of Pestiviruses in Microcephaly" *Lancet*, 1(8539):972-973 (1987).
Cornberg, et al. "Hepatitis C: therapeutic perspectives." *Forum (Genova)*, 11(2):154-162 (2001).
Dymock, et al. Novel approaches to the treatment of hepatitis C virus infection: *Antivir. Chem. Chemother.* 11(2):79-96 (2000).

* cited by examiner

*Primary Examiner*—Laura L. Stockton
(74) *Attorney, Agent, or Firm*—Foley & Lardner LLP; Junrui Yang

(57) ABSTRACT

Disclosed are compounds, compositions and methods for treating Flaviviridae family virus infections.

8 Claims, No Drawings

NITROGEN-CONTAINING HETEROARYL DERIVATIVES

CROSS-REFERENCE TO RELATED APPLICATIONS

This application claims the benefit of U.S. Provisional Application Ser. No. 60/476,141, filed on Jun. 4, 2003, which application is incorporated herein in its entirety.

BACKGROUND OF THE INVENTION

1. Field of the Invention

The invention relates to the field of pharmaceutical chemistry, in particular to compounds, compositions and methods for treating viral infections in mammals mediated, at least in part, by a virus in the flaviviridae family of viruses.

REFERENCES

The following publications are cited in this application as superscript numbers:

1. Giangaspero, et al., Arch. Virol. Suppl., 7: 53-62 (1993);
2. Giangaspero, et al., Int. J. STD. AIDS, 4(5): 300-302 (1993);
3. Yolken, et al., Lancet, 1(8637): 517-20 (1989);
4. Wilks, et al., Lancet, 1(8629): 107 (1989);
5. Giangaspero, et al., Lancet, 2: 110 (1988);
6. Potts, et al., Lancet, 1(8539): 972-973 (1987);
7. Cornberg, et al., "Hepatitis C: therapeutic perspectives." Forum (Genova), 11(2): 154-62 (2001);
8. Dymock, et al., Antivir. Chem. Chemother. 11(2): 79-96 (2000);
9. Devos, et al., International Patent Application Publication No. WO 02/18404 A2, published 7 Mar., 2002;
10. Sommadossi, et al., International Patent Application Publication No. WO 01/90121, published 23 May, 2001;
11. Carroll, S. S., et al., International Patent Application Publication No. WO 02/057287, published 25 Jul., 2002;
12. Carroll, S. S., et al., International Patent Application Publication No. WO 02/057425, published 25 Jul., 2002.

All of the above publications and applications are herein incorporated by reference in their entirety to the same extent as if each individual publication or application was specifically and individually indicated to be incorporated by reference in its entirety.

2. State of the Art

The Flaviviridae family of viruses is composed of three genera: pestivirus, flavivirus and hepacivirus (hepatitis C virus). Of these genera, flaviviruses and hepaciviruses represent important pathogens of man and are prevalent throughout the world. There are 38 flaviviruses associated with human disease, including the dengue fever viruses, yellow fever virus and Japanese encephalitis virus. Flaviviruses cause a range of acute febrile illnesses and encephalitic and hemorrhagic diseases. Hepaciviruses currently infect approximately 2 to 3% of the world population and cause persistent infections leading to chronic liver disease, cirrhosis, hepatocellular carcinoma and liver failure. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients. [1-6]

Currently, there are no antiviral pharmaceutical drugs to prevent or treat pestivirus or flavivirus infections. For hepacivirus, i.e, hepatitis C virus (HCV) infections, interferon alpha (IFN) is currently the only approved drug in the United States. HCV is a major causative agent for post-transfusion and for sporadic non-A, non-B hepatitis. Infection by HCV is insidious in a high proportion of chronically infected (and infectious) carriers who may not experience clinical symptoms for many years.

At present, the only acceptable treatment for chronic HCV is interferon (IFN-alpha) and this requires at least six (6) months of treatment and/or ribavarin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1H-1,2,4-triazole-3-carboxamide), an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of PEG-IFN plus ribavirin. However, a number of patients still have significant side effects, primarily related to ribaviran. Ribavirin causes significant hemolysis in 10-20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. NS3/4A serine protease, ribonucleic acid (RNA) helicase, RNA-dependent RNA polymerase are considered as potential targets for new drugs.[7,8]

Devos, et al.[9] describes purine and pyrimidine nucleoside derivatives and their use as inhibitors of HCV RNA replication. Sommadossi, et al.[10] describes 1', 2' or 3'-modified nucleosides and their use for treating a host infected with HCV. Carroll, et al.[11,12], describe nucleosides as inhibitors of RNA-dependent RNA viral polymerase.

Given the fact of the worldwide epidemic level of HCV and other members of the Flaviviridae family of viruses, there is a strong need for new effective drugs for treatment of flaviviridae family viruses. The present invention provides compounds for treating such infections.

SUMMARY OF THE INVENTION

This invention is directed to novel compounds that are useful in the treatment of viral infections in mammals mediated at least in part by a member of the flaviviridae family viruses such as HCV. Specifically, the compounds of this invention are represented by formula (I):

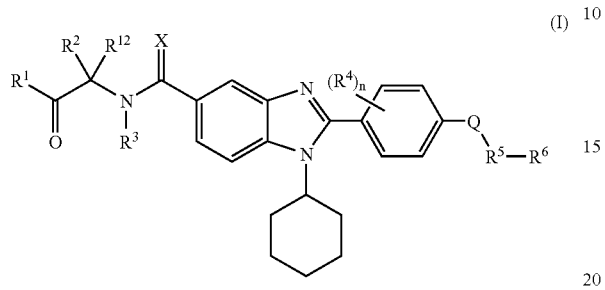
(I)

wherein:
- $R^1$ is selected from the group consisting of —$OR^7$, and —$NR^8R^9$;
- where $R^7$ is selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic;
- $R^8$ and $R^9$ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, $R^8$ and $R^9$, together with the nitrogen atom pendent thereto, form a heterocyclic or substituted heterocyclic ring group;
- $R^2$ and $R^{12}$ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic, and substituted heterocyclic; or, $R^2$ and $R^{12}$, together with the carbon atom pendent thereto, form a cycloalkyl, substituted cycloalkyl, heterocyclic or substituted heterocyclic ring group;
- $R^3$ is selected from the group consisting of hydrogen and alkyl; or $R^2$ and $R^3$, together with the carbon atom pendent to $R^2$ and the nitrogen atom pendent to $R^3$, form a heterocyclic or substituted heterocyclic ring group;
- each $R^4$ is independently selected from the group consisting of halo, nitro, amino, substituted amino, cyano and hydroxyl;
- Q is selected from the group consisting of —O—, —$S(O)_q$— and —$N(R^3)$— where $R^3$ is as defined above and q is zero, one or two;
- X is selected from the group consisting of oxygen, sulfur, and =$NR^{11}$, where $R^{11}$ is hydrogen or alkyl;
- $R^5$ is alkylene or substituted alkylene;
- $R^6$ is selected from the group consisting of aryl, substituted aryl, heteroaryl, and substituted heteroaryl; and
- n is 0 to 3;

or pharmaceutically acceptable salts thereof.

In one embodiment $R^{12}$ is H and $R^2$ is the side chain of an amino acid, and preferably an L-amino acid.

In one embodiment, the compounds of Formula I have the structure of Formula Ia below:

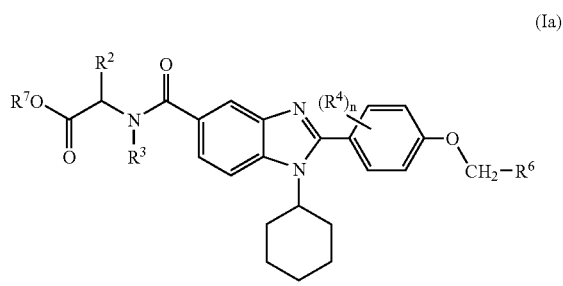
(Ia)

wherein $R^2$, $R^3$, $R^4$, $R^6$, $R^7$ and n are as defined above.

Still other preferred embodiments of the invention are represented by compounds of Formula Ib below:

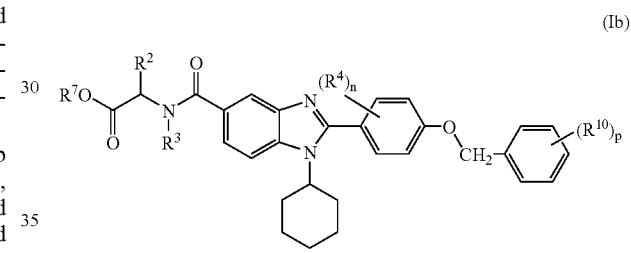
(Ib)

wherein $R^2$, $R^3$, $R^4$, $R^7$ and n are as defined above,
- each $R^{10}$ is independently selected from the group consisting of alkyl, substituted alkyl, aryl, substituted aryl, heteroaryl, substituted heteroaryl, carboxyl, carboxyl ester, and —$C(O)NR^8R^9$ where $R^8$ and $R^9$ are as defined above; and
- p is 0 to 5, or pharmaceutically acceptable salts thereof.

In another embodiment of the invention, the compounds of the present invention are repreented by Formula II below:

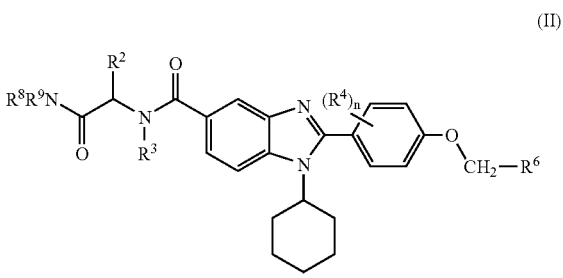
(II)

wherein $R^2$, $R^3$, $R^4$, $R^6$, $R^8$, $R^9$, and n are as defined above, or pharmaceutically acceptable salts thereof.

In yet another embodiment, the compounds of the present invention are represented by Formula III below:

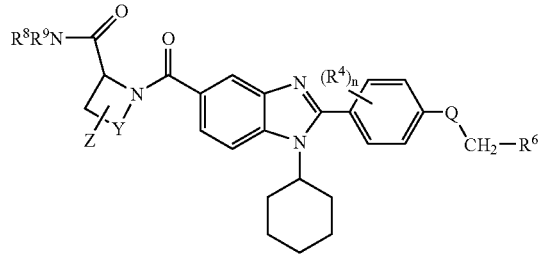

(III)

wherein R⁴, R⁶, R⁸, R⁹, and n are as defined above, Z is selected from the group consisting of hydrogen, hydroxy, halo, alkyl, and aryl, and Y is selected from the group consisting of —CH₂—, —CH₂CH₂—, —CH₂CH₂CH₂—, —CH₂CH₂O— (morpholino), —CH₂CH₂S— (thiomorpholino), —CH₂CH₂NH— (piperazinyl) or pharmaceutically acceptable salts thereof.

In another embodiment of the invention, the compounds of the present invention represented by Formula IV below:

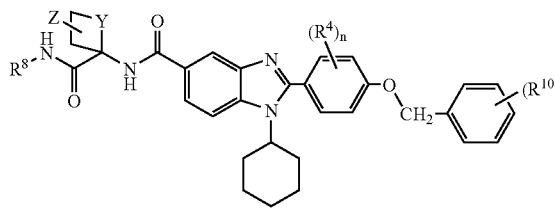

(IV)

wherein Z, Y, R⁴, R⁸, R¹⁰, p and n are as defined above, or pharmaceutically acceptable salts thereof.

Representative compounds for this application are presented in the Tables below.

TABLE 1

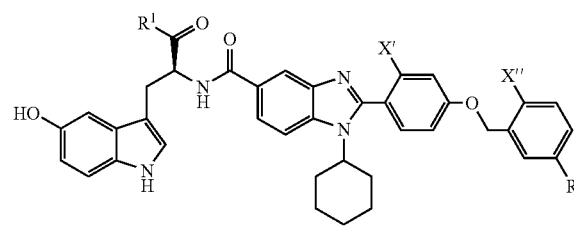

| Ex No | Comp No. | R¹ | X' | X'' | R' |
|---|---|---|---|---|---|
| 1 | 61 | —OH | F | 4-Cl-φ- | —C(O)NH₂ |
| 2 | 64 | —OH | F | 4-Cl-φ- | —C(O)-(4-hydroxypiperiz-N-yl) |
| 3 | 65 | —OH | F | Br | —C(O)-(4-hydroxypiperiz-N-yl) |
| 4 | 66 | —OH | F | H | —C(O)-(4-hydroxypiperiz-N-yl) |
| 5 | 76 | —OH | H | H | H |
| 6 | 77 | —NH₂ | H | H | H |

TABLE 2

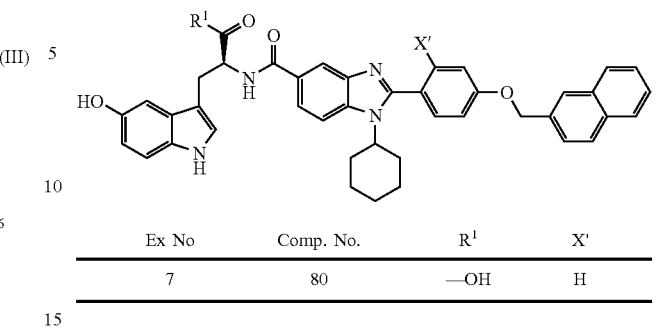

| Ex No | Comp. No. | R¹ | X' |
|---|---|---|---|
| 7 | 80 | —OH | H |

TABLE 3

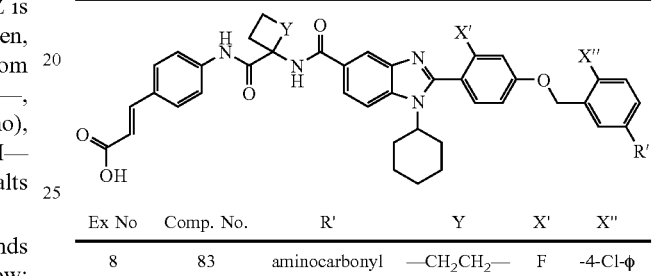

| Ex No | Comp. No. | R' | Y | X' | X'' |
|---|---|---|---|---|---|
| 8 | 83 | aminocarbonyl | —CH₂CH₂— | F | -4-Cl-φ |

Compounds included within the scope of this invention include, for example, those set forth below (including pharmaceutically acceptable salts thereof):

2-{[2-(4-benzyloxy-phenyl)-1-cyclohexyl-1H-benzimidazole-5-carbonyl]-amino}-3-(5-hydroxy-1H-indol-3-yl)-propionic acid (Compound 76);

2-[(1-cyclohexyl-2-{2-fluoro-4-[3-(aminocarbonyl)-6-(4-chlorophenyl)benzyloxy]-phenyl}-1H-benzimidazole-5-carbonyl)-amino]-3-(5-hydroxy-1H-indol-3-yl)-propionic acid (Compound 61);

2-[(2-{4-[2-bromo-5-(4-hydroxyl-piperidine-1-carbonyl)-benzyloxy]-2-fluoro-phenyl}-1-cyclohexyl-1H-benzimidazole-5-carbonyl)-amino]-3-(5-hydroxy-1H-indol-3-yl)-propionic acid (Compound 65);

2-[(1-cyclohexyl-2-{2-fluoro-4-[3-(4-hydroxyl-piperidine-1-carbonyl)-benzyloxy]-phenyl}-1H-benzimidazole-5-carbonyl)-amino]-3-(5-hydroxy-1H-indol-3-yl)-propionic acid (Compound 66);

2-(4-benzyloxy-phenyl)-1-cyclohexyl-1H-benzimidazole-5-carboxylic acid [1-carbamoyl-2-(5-hydroxy-1H-indol-3-yl)-ethyl]-amide (Compound 77);

2-[(2-{4-[4'-chloro 4-(4-hydroxyl-piperidine-1-carbonyl)-biphen-2-ylmethoxy]-2-fluoro-phenyl}-1-cyclohexyl-1H-benzoimidazole-5-carbonyl)-amino]-3-(5-hydroxy-1H-indol-3-yl)-propionic acid (Compound 64);

2-({1-cyclohexyl-2-[4-(naphthalene-2-ylmethoxy)-phenyl]-1H-benzimidazole-5-carbonyl}-amino)-3-(5-hydroxy-1H-indol-3-yl)-propionic acid (Compound 80); and 3-(4-{[1-({2-[4-(4-Carbamoyl-4'-chloro-biphen-2-ylmethoxy)-2-fluoro-phenyl]-1-cyclohexyl-1H-benzoimidazole-5-carbonyl}-amino)-cyclopentanecarbonyl]-amino}-phenyl)-acrylic acid (Compound 83).

In still another embodiment of the invention, a pharmaceutical composition is provided comprising a pharmaceutically acceptable diluent and a therapeutically effective amount of one or more of the compounds described herein.

In yet another embodiment of the invention, methods of treating or preventing viral infections in mammals are provided wherein the viral infection is mediated, at least in part, by a member of the flaviviridae family viruses, such as HCV, said method comprising administering to a patient in need thereof, a pharmaceutical composition as described above.

In yet another embodiment of the invention, methods of treating or preventing viral infections in mammals are provided wherein the compounds of this invention are administered in combination with the administration of a therapeutically effective amount of one or more agents active against HCV. Active agents against HCV include ribavirin, levovirin, thymosin alpha-1, an inhibitor of NS3 serine protease, and inhibitor of inosine monophosphate dehydrogenase, interferon-alpha, pegylated interferon-alpha, alone or in combination with ribavirin or levovirin. Prefereably the additional agent active against HCV is interferon-alpha or pegylated interferon-alpha alone or in combination with ribavirin or levovirin.

DETAILED DESCRIPTION OF THE INVENTION

The invention is directed to compounds, compositions and methods for treating flaviviridae family viral infections. However, prior to describing this invention in detail, the following terms will first be defined:

Definitions

Before the present invention is described in detail, it is to be understood that, unless otherwise indicated, this invention is not limited to any particular composition or pharmaceutical carrier, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "pharmaceutically acceptable diluent" in a composition includes two or more pharmaceutically acceptable diluents, and so forth.

In this specification and in the claims that follow, reference will be made to a number of terms that shall be defined to have the following meanings:

As used herein, "alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents independently selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

As used herein, "alkylene" refers to divalent alkyl groups having from 1 to 10 carbon atoms, preferably from 1 to 5 carbon atoms and more preferably 1 to 3 carbon atoms. This term is exemplified by groups such as methylene, ethylene, n-propylene, n-butylene, and the like.

"Substituted alkylene" refers to an alkylene group having from 1 to 3, and preferably 1 to 2, substituents independently selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom pendent thereto, a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Alkenyl" refers to alkenyl group preferably having from 2 to 6 carbon atoms and more preferably 2 to 4 carbon atoms and having at least 1 and preferably from 1 to 2 sites of alkenyl unsaturation.

"Substituted alkenyl" refers to alkenyl groups having from 1 to 3 substituents, and preferably 1 to 2 substituents, independently selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not pendent to a vinyl carbon atom.

"Alkynyl" refers to alkynyl group preferably having from 2 to 6 carbon atoms and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, independently selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not pendent to acetylenic carbon atom.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto, to form a heterocyclic or substituted heterocylic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR'"C(O)alkyl, —NR'"C(O)substituted alkyl, —NR'"C(O)-cycloalkyl, —NR'"C(O)substituted cycloalkyl, —NR'"C(O)alkenyl, —NR'"C(O)substituted alkenyl, —NR'"C(O)alkynyl, —NR'"C(O)substituted alkynyl, —NR'"C(O)aryl, —NR'"C (O)substituted aryl, —NR'"C(O)heteroaryl, —NR'"C(O) substituted heteroaryl, —NR'"C(O)heterocyclic, and —NR'"C(O)substituted heterocyclic where R'" is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is on an aromatic carbon atom. Preferred aryls include phenyl and naphthyl.

"Substituted aryl" refers to aryl groups which are substituted with from 1 to 3 substituents, and preferably 1 to 2 substituents, independently selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts therof.

"Carboxyl esters" refers to the groups —C(O)O-alkyl, —C(O)O-substituted alkyl, —(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl group, having from 1 to 5 substituents independently selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 15 carbon atoms, preferably from 1 to 10 carbon atoms, and 1 to 4 heteroatoms selected from the group consisting of oxygen, nitrogen and —S(O)$_q$ (where q is zero, one or two) within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl, thiophenyl, and furyl.

"Substituted heteroaryl" refers to heteroaryl groups that are substituted with from 1 to 3 substituents independently selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is to a heterocyclic ring atom.

"Substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5, 6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

The term "amino acid" refers to α-amino acids of the formula HR$^{19}$NCH(R$^2$)COOH where R$^2$ is as defined above as a chain of an amino acid and R$^{19}$ is hydrogen, alkyl, substituted alkyl or aryl.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The following synthetic protocols illustrate the general manner for preparing the compounds described herein. Specifically, synthetic Scheme 1 below illustrates one method for the preparation of compounds of this invention.

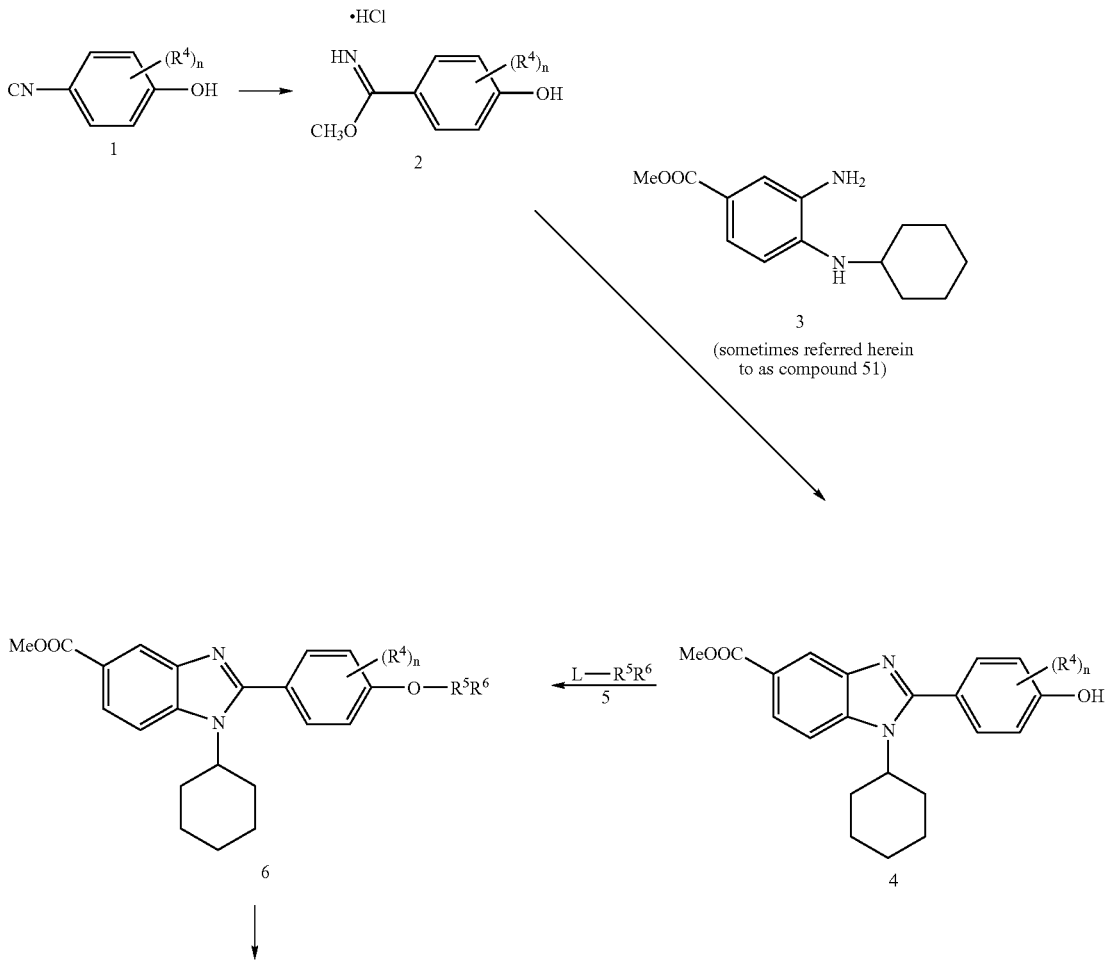

-continued

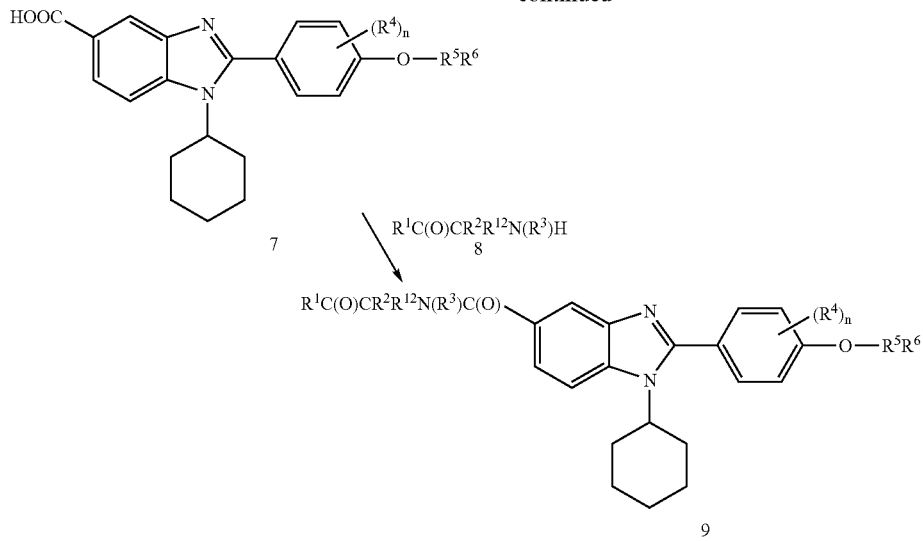

where $R^1$, $R^2$, $R^3$, $R^4$, $R^5$, $R^6$, $R^{12}$ and n, are as defined above and L is a leaving group.

In Scheme 1 above, optionally substituted p-cyanophenol, compound 1, is converted to the corresponding methoxyimide hydrochloride salt, compound 2, by contacting compound 1 with anhydrous HCl in methanol. The reaction is conducted under conventional conditions preferably at a temperature of from about 0° C. to room temperature. The reaction is continued until it is substantially complete which typically occurs within about 1 to 12 hours. Upon reaction completion, the resulting methoxyimide hydrochloride salt, compound 2, can be recovered by conventional techniques such as extraction, filtration, precipitation, and the like; or, alternatively, used in the next step without purification and/or isolation.

Methoxyimide hydrochloride salt, compound 2, is then contacted with at least a stoichiometric equivalent of methyl 3-amino-4-cyclohexylaminobenzoate, compound 3, under conditions to effect ring formation. The reaction is preferably conducted under an inert atmosphere in a protic solvent such as anhydrous methanol, anhydrous ethanol and the like at an elevated temperature of from about 50° to about 75° C. and preferably at reflux. The reaction is continued until it is substantially complete which typically occurs within about 1 to 24 hours. Upon reaction completion, the resulting 2-(optionally substituted p-hydroxy-phenyl)benzimidazole, compound 4, can be recovered by conventional techniques such as neutralization, extraction, precipitation, chromatography, filtration and the like; or, alternatively, used in the next step without purification and/or isolation.

Alternatively, this step of the reaction sequence can utilize commercially available 4-hydroxybenzaldehyde (not shown) in combination with compound 3. The reaction is conducted in a suitable solvent such DMF in the presence of a small amount of water and Oxone®. The reaction is preferably conducted at an elevated temperature of from about 0° to about 40° C. The reaction is continued until it is substantially complete which typically occurs within about 1 to 10 hours. Upon reaction completion, compound 4 can be recovered by conventional techniques such as neutralization, extraction, precipitation, chromatography, filtration and the like; or, alternatively, used in the next step without purification and/or isolation.

2-(Optionally substituted p-hydroxyphenyl)benzimidazole, compound 4, is then derivatized to the corresponding substituted alkoxy derivative, compound 6, by methods well known in the art. In one preferred method, compound 4 is contacted with a suitable alkali or alkaline earth metal base, such as potassium carbonate, in an inert diluent, such as DMF, acetone, 2-butanone and the like, to form the alkali or alkaline earth metal salt of the hydroxyl group. This salt is generally not isolated, but is reacted in situ with at least one equivalent of a substituted alkyl compound, L-$R^5$—$R^6$ (where L is a leaving group, such as chloro, bromo, iodo, mesylate, tosylate and the like), to afford the ether. The reaction is preferably conducted at an elevated temperature of from about 50° to about 100° C. The reaction is continued until it is substantially complete which typically occurs within about 1 to 10 hours. Upon reaction completion, the corresponding alkoxide derivative, compound 6, can be recovered by conventional techniques such as neutralization, extraction, precipitation, chromatography, filtration and the like; or, alternatively, used in the next step without purification and/or isolation.

Examples of substituted alkyl halides for use in this reaction include, but are not limited to, (1-bromoethyl) benzene, t-butyl 3-(bromomethyl)-4-bromobenzoate, methyl 4-bromobenzoate, and the like. In a preferred embodiment, when the substituted alkyl halide is substituted with a carboxyl group, this group is orthogonally protected as compared to the carboxyl group directly attached to the benzimidazole group. Such orthogonal protection permits this carboxyl group to be differentially derivatized relative to the carboxyl group directly attached to the benzimidazole group.

The methyl carboxyl ester of compound 6 is then converted to the corresponding acid functionality by conventional hydrolysis procedures to provide for compound 7 which can be recovered by conventional techniques such as neutralization, extraction, precipitation, chromatography, filtration and the like; or, alternatively, used in the next step without purification and/or isolation.

The acid functionality of compound 7 is then coupled to the primary or secondary amino group of compound 8 using conventional coupling conditions well known in the art. For example, this coupling reaction can be conducted using well-known coupling reagents such as carbodiimides, BOP reagent (benzotriazol-1-yloxy-tris (dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxy-benzotriazole, pentafluorophenyl trifluoroacetate, and the like, may be used to facilitate the coupling reaction. When necessary, a suitable base such as N,N-diisopropylethyl amine can be used to scavenge the acid generated during the reaction.

This coupling reaction is typically conducted by contacting compound 7 with about 1 to about 2 equivalents of the coupling reagent and at least one equivalent, preferably about 1 to about 1.2 equivalents, of compound 8 in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, compound 9 is recovered by conventional methods including neutralization, extraction, precipitation, chromatography, filtration, and the like.

The starting materials employed in Scheme 1 are either well known in the art or can be prepared by art recognized methods. For example, many examples of compound 1 are commercially available including, by way of example only, 4-cyanophenol, 2-chloro-4-hydroxybenzonitrile, 2-fluoro-4-hydroxybenzonitrile, 4-hydroxy-3-methoxybenzonitrile, etc. which are commercially available from Aldrich Chemical Company, Milwaukee, Wis., USA. Derivatization of such compounds or other known 4-cyanophenols using well known chemistry provides facile routes for the preparation of a varierty of compounds within compound 1.

To provide for compounds of this invention where Q is sulfur, thiol groups can prepared from the reaction between aryl halides and NaSH or between diazonium salts and NaSH.

Likewise, commercially available 3,4-dihydroxybenzonitrile can be selectively protected using conventional techniques to provide for a 3-hydroxy-4-PgO-benzonitrile (Pg is a protecting group). The 3-hydroxy group can then be modified as desired using well known chemistry to provide for a variety of derivatives including, by way of example only, alkoxy groups, aryloxy groups, heteroaryloxy groups, esters, carbamate groups, carboxyl groups (e.g., the hydroxyl group is converted to a halo group as shown below and the halo group is then converted to the carboxyl group by formation of a Grinard reagent followed by addition of carbon dioxide using well known chemistry), and the like. Subsequently, the protecting group, Pg, is removed and the derivatized compound used in Scheme 1.

For compounds of Formula I where Q is —N(R³)—, these compounds are readily prepared from the corresponding 4-aminobenzonitrile compounds and derivatives thereof. For example, both 4-aminobenzonitrile and 4-amino-2-chlorobenzonitrile are commercially available. The chloro group of the latter compound can be optionally derivatized as described above to provide for a variety of derivatives. Additionally, the amino group can be optionally monoalkylated by methods well known in the art. It is understood, however, that blocking group may be required to shield the amino group from undesired reactions until the amino group is to be coupled to compound 3. Such coupling is well known in the art. When L is a halo group such as benzyl bromide, the reaction will typically include a suitable base such as diisopropylethylamine (DIEA) to scavenge the acid generated.

Regarding the 3-amino-4-cyclohexylaminobenzoates, compound 3, these compounds can be readily prepared by procedures well known in the art. One preferred method for preparation is set forth in synthetic Scheme 2 as follows:

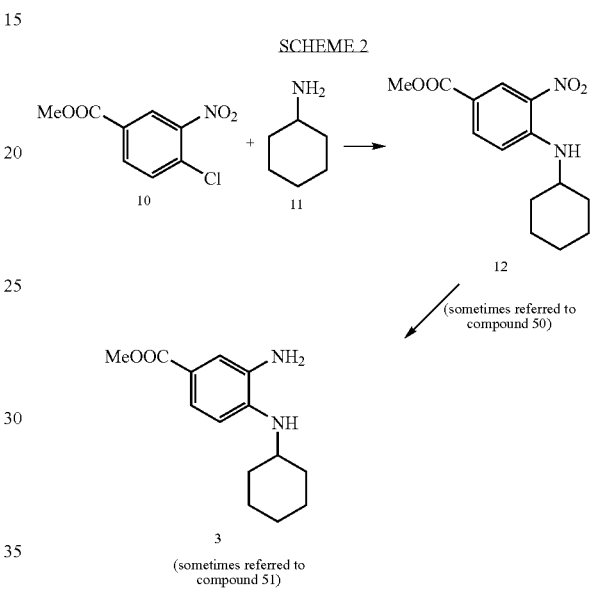

Specifically, in Scheme 2, methyl 4-chloro-3-nitrobenzoate, compound 10, (which is prepared by reaction of commercially available 4-chloro-3-nitrobenzoic acid and methanol with a catalytic amount of an acid, such as HCl) is combined with from 1 to 3 equivalents of commercially available cyclohexylamine, compound 11, under conventional coupling conditions. The reaction is preferably conducted in an inert solvent such as DMSO at an elevated temperature of from about 30° to about 75° C. The reaction is continued until it is substantially complete which typically occurs within about 1 to 48 hours. Upon reaction completion, the resulting methyl 4-cyclohexylamino-3-nitrobenzoate, compound 12 (sometimes referred to herein as compound 50), can be recovered by conventional techniques such as neutralization, extraction, precipitation, chromatography, filtration and the like; or, alternatively, used in the next step without purification and/or isolation.

The nitro group of compound 12 is then hydrogenated under conventional conditions to provide for the corresponding methyl 4-cyclohexylamino-3-aminobenzoate, compound 3, which can be recovered by conventional techniques such as neutralization, extraction, precipitation, chromatography, filtration and the like. Compound 3 is sometimes referred to herein as compound 51.

Similarly, compound 5 represents a group of compounds well known in the art which are either commercially available or can be prepared by art recognized techniques. For example, suitable commercially available compounds includes, for instance, benzyl bromide, 1-bromoethylbenzene, 2-methoxybenzyl chloride, 3-methoxybenzyl-chloride, 4-methoxybenzyl chloride, 2-chlorobenzyl bromide, 3-chlorobenzyl bromide, 4-chlorobenzyl bromide, and the like. In addition, derivativization of commercially available compounds using methods well known in the art can be used to provide for suitable compounds useful as compound 5 in Scheme 1. One example of such derivatization techniques are set forth in Scheme 3 as follows:

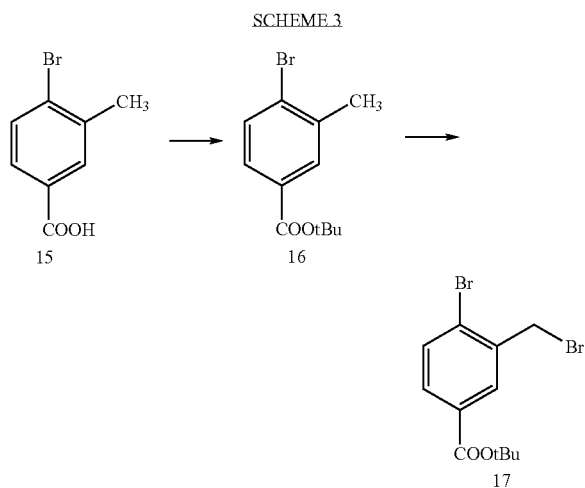

In Scheme 3, commercially available 4-bromo-3-methylbenzoic acid, compound 15, is converted under anhydrous conditions and further under an inert atmosphere to the corresponding t-butyl ester by conventional methods using oxalyl chloride in a solvent combination of DMF and methylene chloride. Upon formation of the anhydride (not shown), conversion to the t-butyl ester, compound 16 (sometimes referred to herein as compound 54) is achieved by contact an excess of the potassium t-butoxide in THF. The reaction is typically conducted at from about 0° C. to about 40° C. for a period of time to effect reaction completion which preferably is achieved in about 1 to 10 hours. Upon reaction completion, the resulting t-butyl 4-bromo-3-methylbenzoate, compound 16, can be recovered by conventional techniques such as neutralization extraction, precipitation, chromatography, filtration and the like; or, alternatively, used in the next step without purification and/or isolation.

Compound 16 is then contacted with a molar excess of both the alpha, alpha-azoisobutyronitrile (AIBN) and N-bromosuccinimide (NBS). The reaction is maintained at an elevated temperature, preferably at reflux, until reaction completion which preferably is achieved in about 10 to 24 hours. Upon reaction completion, the resulting t-butyl 4-bromo-3-bromomethylbenzoate, compound 17 (sometimes referred to herein as compound 55), can be recovered by conventional techniques such as neutralization, extraction, precipitation, chromatography, filtration and the like; or, alternatively, used in the next step without purification and/or isolation.

Other derivatization procedures using well known chemistry and readily available starting materials will be readily apparent to the skilled artisan.

The amino acids or amino acid amides represented by compound 8 are either known compounds or compounds that can be prepared from known compounds by conventional synthetic procedures. Examples of suitable amino acids for use in this reaction include, but are not limited to, tryptophan, 5-hydroxytryptophan, glycine, tyrosine, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-indoline-2-carboxylic acid, L-1,2,3,4-tetrahydroisoquinoline-3-carboxylic acid, L-thiazolidine-4-carboxylic acid, L-(5,5-dimethyl)thiazolidine-4-carboxylic acid, L-thiamorpholine-3-carboxylic acid, glycine, 2-tert-butylglycine, D,L-phenylglycine, L-alanine, N-methylalanine, N-methyl-L-phenylalanine, L-diphenylalanine, sarcosine, D,L-phenylsarcosine, L-aspartic acid-tert-butyl ester, L-glutamic acid-tert-butyl ester, L-(O-benzyl)serine, 1-aminocyclopropanecarboxylic acid, 1-aminocyclobutanecarboxylic acid, 1-aminocyclopentanecarboxylic acid (cycloleucine) 1-aminocyclohexanecarboxylic acid, L-serine and the like. If desired, the corresponding carboxylic acid esters of the amino acids, such as the methyl esters, ethyl esters and the like, can be employed in the above reaction. Subsequent hydrolysis of the ester group to the carboxylic acid using conventional reagents and conditions, i.e., treatment with an alkali metal hydroxide in an inert diluent such as methanol/water then provides the free acid or acid salt of a compound of Formula I. In addition, conventional amidation procedures can be used to effect amidation of the carboxylic acid. Such procedures entail reaction of the acid or activated form thereof with a suitable amine under conditions to effect amidation.

Utility, Testing, and Administration

Utility

The present invention provides novel compounds possessing antiviral activity, including flaviviridae family viruses such as hepatitis C virus. The compounds of this invention inhibit viral replication by inhibiting the enzymes involved in replication, including RNA dependent RNA polymerase. They may also inhibit other enzymes utilized in the activity or proliferation of flaviviridae viruses.

Compounds of this invention maybe used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula I, Ia, Ib, II, III or IV may range from approximately 0.1 to 20 mg per kilogram body weight of the recipient per day, more preferably from about 0.1 to 10 mg/kg/day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I, Ia, Ib, II, III or IV in combination with at least one pharmaceutically acceptable excipient. Acceptable excipients are non-toxic, aid administration, and do not adversely affect the therapeutic benefit of the compound of Formula I, Ia, Ib, II, III or IV. Such excipients may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include sterile water, sterile saline, sterile aqueous dextrose, and sterile glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula I, Ia, Ib, II, III or IV based on the total formulation, with the balance being one or more suitable pharmaceutical excipients. Preferably, the compound is present at a level of about 1-80 wt %. Representative pharmaceutical formulations containing a compound of Formula I, Ia, Ib, II, III or IV are described below.

EXAMPLES

In the examples below, the following abbreviations have the following meanings. If an abbreviation is not defined, it has its generally accepted meaning.

AIBN=α,α-azoisobutyronitrile
aq.=aqueous
BOP=Benzotriazol-1-yloxy-tris(dimethylamino)phosphonium hexafluorophosphate
DCC=dicyclohexylcarbodiimide
DIEA=N,N-diisopropylethylamine
DMEM=Dulbeco's Modified Eagle's Medium
DMF=N,N-dimethylformamide
DMSO=dimethylsulfoxide
ESI=electrospray ionization
g=gram
h=hours
HPLC=high performance liquid chromatography
M=molar
M+H$^+$=parent mass spectrum peak plus H+
mM=millimolar
MeOH=methanol
mg=milligram
min.=minutes
mL=milliliter
mmol=millimole
MS=mass spectrum
N=normal
pfp=pentafluorophenyl radical
ph or φ=phenyl
psi=pounds per square inch
t-Bu=t-butyl protecting group
TFA=trifluoroacetic acid
THF=tetrahydrofuran μL=microliters
nm=nanometer
nM=nanomolar
NBS=N-bromosuccinimide
NTA=Nitrilotriacetic acid
NTP=Nucleotide triphosphate
mM=millimolar
DTT=Dithiothreitol
EDTA=Ethylenendiamine tetraacetic acid
IU=International units
μg=microgram
HBTU=O-benzotriazole-1-yl-N,N,N',N'-tetramethyluronium hexafluorophosphate Set forth in the examples below are compounds and intermediates useful for making compounds of the present invention.

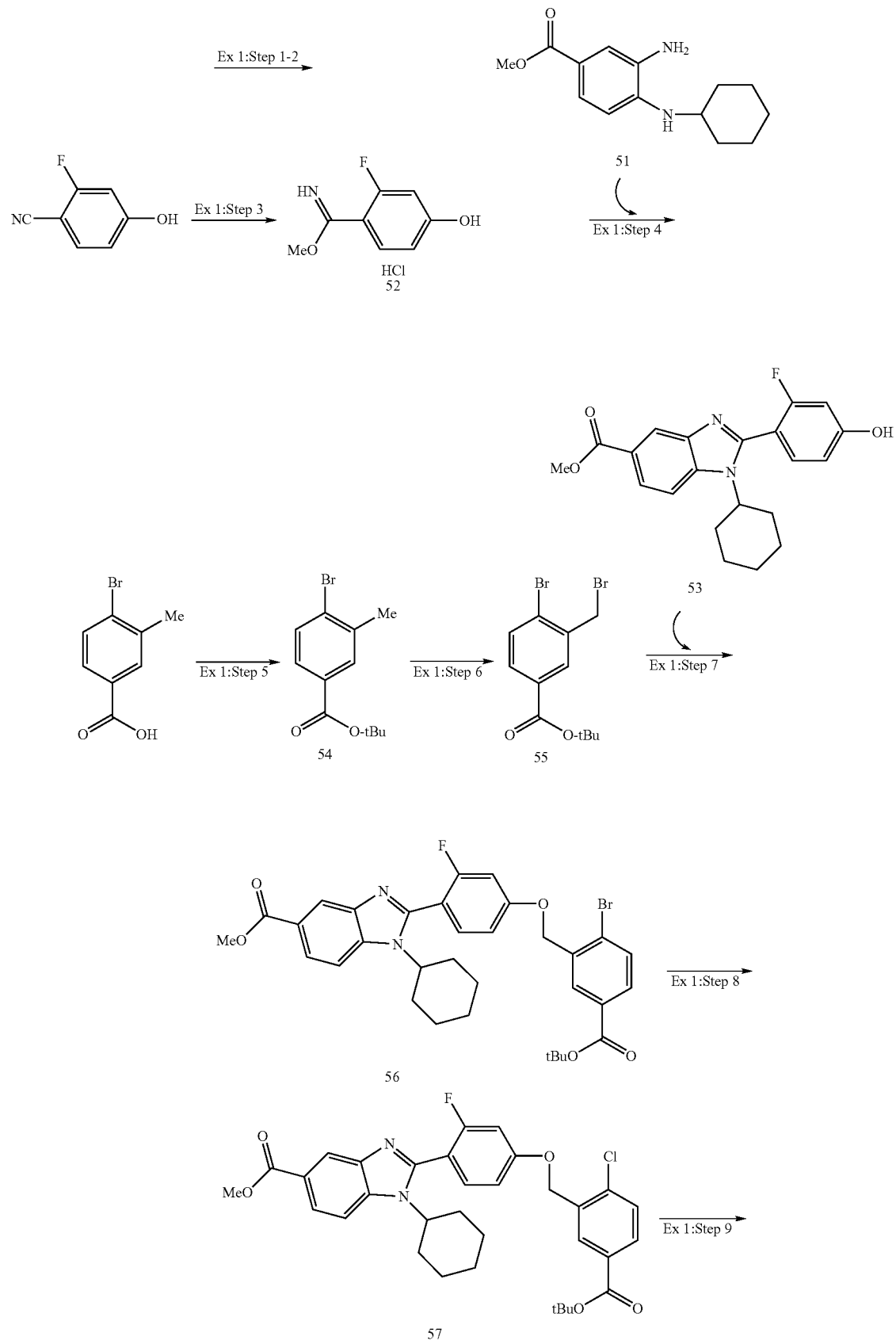

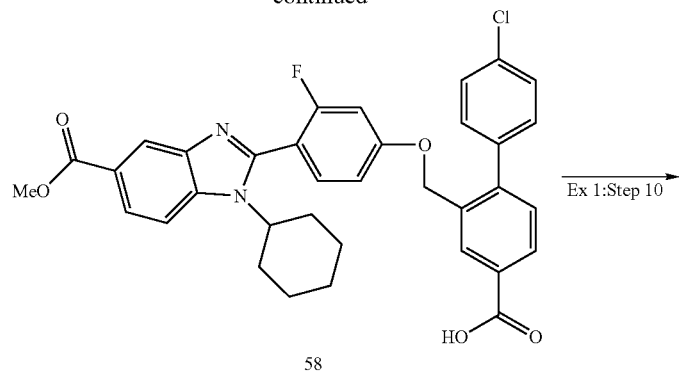
58
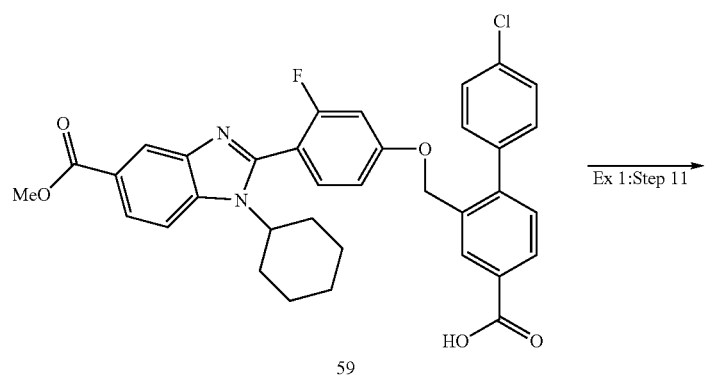
59
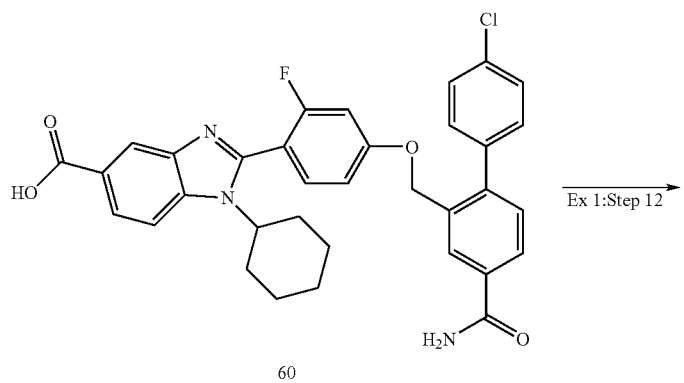
60
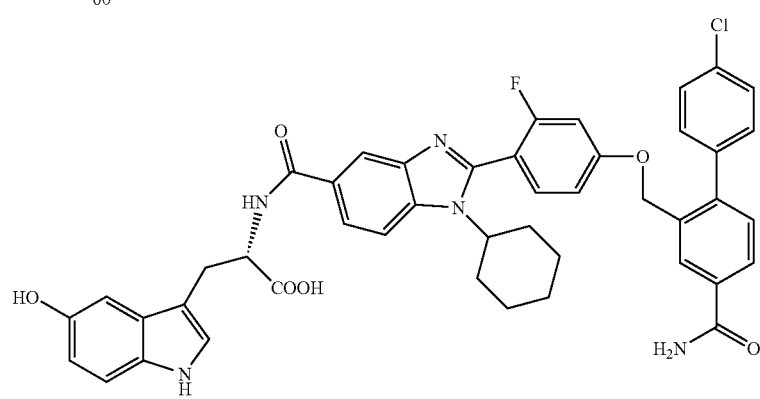
61

Example 1

Preparation of 2-({2-[4-(4-Carbamoyl-4'-chloro-biphen-2-ylmethoxy)-2-fluoro-phenyl]-1-cyclohexyl-1H-benzimidazole-5-carbonyl}-amino)-3-(5-hydroxy-1H-indol-3-yl)-propionic acid hydrochloride (Compound 61)

Scheme 1 Above Corresponds to the Following Procedures

1. 4-Cyclohexylamino-3-nitrobenzoic acid methyl ester (Compound 50)

Methyl 4-chloro-3-nitrobenzoate (25 g, 0.116 mol) was dissolved in DMSO (75 mL) and cyclohexylamine (25 mL, 0.243 mol) was added. The mixture was stirred at 60° C. for 24 h, and diluted with water. The precipitates were collected by filtration, washed with water and dried to give compound 50 (32.2 g, 99%). MS (ESI) 279.13 (M+H$^+$).

2. 3-Amino-4-cyclohexylamino-benzoic acid methyl ester (Compound 51 or Compound 3 as Noted Above)

Compound 50 (10.57 g, 37.9 mol) was hydrogenated in MeOH (130 mL) over 5% Pd/C (150 mg) under H$_2$ for 30 minutes. The reaction was filtered through Celite and the solution was evaporated to give a brown solid (9.4 g, 99%). MS (ESI) 249.17 (M+H$^+$).

3. 2-Fluoro-4-hydroxy-benzimidic acid methyl ester (Compound 52)

2-Fluoro-4-hydroxybenzonitrile (3.55 g, 25.89 mmol) was dissolved in anhydrous MeOH (100 mL) and the solution was bubbled with anhydrous hydrogen chloride at 0° C. for 1 h and at room temperature for further 1 h. After evaporation of solvent, the solid residue was dried under high vacuum for 2 h to give a crude compound 52, which was directly used in next step reaction.

4. 1-Cyclohexyl-2-(2-fluoro-4-hydroxyphenyl)-1H-benzimidazole-5-carboxylic acid methyl ester (Compound 53)

The crude compound 52 was dissolved in anhydrous MeOH (150 mL). Compound 51 (4.0 g, 16.11 mmol) was then added. The reaction mixture was stirred under argon at reflux for 16 h and cooled down to room temperature. The precipitates formed were filtered and washed with water and dried under high vacuum to give the compound 53 (3.2 g, 54%). MS (ESI) 369.17 (M+H$^+$).

5. 4-Bromo-3-methyl-benzoic acid tert-butyl ester (Compound 54)

4-Bromo-3-methylbenzoic acid (3.5 g, 16.27 mmol) was suspended in anhydrous dichloromethane (25 mL) under argon. DMF (0.5 mL) was added and followed by addition of oxalyl chloride (1.7 mL) at room temperature. The reaction mixture was stirred at room temperature for 20 min. and oxalyl chloride (0.5 mL) was added dropwise. The mixture was then stirred at room temperature for further 2 h. Solvent was evaporated. The residue was dissolved in anhydrous THF (25 mL) and cooled in an ice-bath. A solution of potassium tert-butoxide (3.65 g, 32.52 mmol) in anhydrous THF (20 mL) was added dropwise at 0° C. The reaction mixture was stirred at room temperature for 1 h, and water (100 mL) was added. The mixture was extracted with EtOAc and organic phase was washed with brine and water, and dried over anhydrous MgSO$_4$. After evaporation of solvent, brown oil was obtained (3.78 g, 86%). MS (ESI) 272.76 (M+H$^+$).

6. 4-Bromo-3-bromomethyl-benzoic acid tert-butyl ester (Compound 55)

A mixture of compound 54 (1.83 g, 6.75 mmol), N-bromosuccinimide (1.38 g, 7.75 mmol) and AIBN (1.27 g, 7.75 mmol) was stirred in carbon tetrachloride (CCl$_4$) at reflux for 16 h and cooled down to room temperature. The reaction mixture was filtered and filtrate was passed through a short column and washed with chloroform. After evaporation of solvent, crystals were obtained (0.23 g, 98%). MS (ESI) 351.65 (M+H$^+$).

7. 2-[4-(2-Bromo-5-tert-butoxylcarbonyl-benzyloxy)-2-fluoro-phenyl]-1-cyclohexyl-1H-benzimidazole-5-carboxylic acid methyl ester (Compound 56)

A mixture of compound 53 (1.0 g, 2071 mmol), compound 55 (1.9 g, 5.43 mmol) and K$_2$CO$_3$ (0.76 g) in anhydrous DMF (40 mL) was stirred at 80° C. for 2 h and cooled down to room temperature. The mixture was filtered and washed with CHCl$_3$. The filtrate was evaporated to dryness. The residue was purified by chromatography eluted with CHCl$_3$—MeOH (50:1) to give compound 56 (0.84 g, 98%). MS (ESI) 639.15, 637.15 (M+H$^+$).

8. 2-[4-(4-tert-Butoxylcarbonyl-4'-chloro-biphen-2-ylmethoxy)-2-fluoro-phenyl]-1-cyclohexyl-1H-benzimidazole-5-carboxylic acid methyl ester (Compound 57)

A mixture of compound 56 (0.45 g, 0.71 mmol), 4-chlorobenzene-boronic acid (0.33 g, 2.11 mmol) and Pd(Ph$_3$P)$_4$ (80 mg) was dissolved in toluene (25 mL) and MeOH (6 mL) under argon. 2 M Aqueous NaHCO$_3$ (2.5 mL) was added. The reaction mixture was stirred at 70° C. under argon for 16 h and cooled down to room temperature. After evaporation of solvent, the residue was purified by chromatography eluted with CHCl$_3$—MeOH (50:1) to yield compound 57 (0.49 g, 96%). MS (ESI) 669.26 (M+H$^+$).

9. 2-[4-(4-Carboxyl-4'-chloro-biphen-2-ylmethoxy)-2-fluoro-phenyl]-1-cyclohexyl-1H-benzimidazole-5-carboxylic acid methyl ester (Compound 58)

To a solution of compound 57 (0.3 g) in anhydrous dichloromethane (10 mL) was added trifluoroacetic acid (10 mL). The mixture was stirred at room temperature for 1 h. After evaporation of solvent, a solid was obtained (0.285 g, 98%). MS (ESI) 611.14 (M−H$^+$).

10. 2-[4-(4-Carbamoyl-4'-chloro-biphen-2-yl-methoxy)-2-fluoro-phenyl]-1-cyclohexyl-1H-benzimidazole-5-carboxylic acid methyl ester (Compound 59)

To a solution of compound 58 (0.18 g, 0.294 mmol) in anhydrous DMF (5 mL) in the presence of N,N-diisopropylethylamine (0.11 mL) was added pfp trifluoroacetate (0.1 mL, 0.588 mmol) dropwise at 0° C. The reaction mixture was stirred at room temperature for 8 h and then 2 M $NH_3$ in 2-propanol (2 mL) was added. The mixture was stirred at room temperature overnight. After evaporation of solvent, the residue was purified by chromatography eluted with $CHCl_3$—MeOH (40:1) to give a solid (0.15 g, 83%). MS (ESI) 612.19 (M+H$^+$).

11. 2-[4-(4-Carbamoyl-4'-chloro-biphen-2-yl-methoxy)-2-fluoro-phenyl]-1-cyclohexyl-1H-benzimidazole-5-carboxylic acid (Compound 60)

Compound 59 (0.12 g, 0.196 mmol) was dissolved in MeOH (6 mL) and 2 M aqueous NaOH (3 mL) was added. The reaction mixture was stirred at 45° C. for 2.5 h and cooled down to 0° C. The mixture was neutralized with 5 N HCl to pH 3. After evaporation of solvent, the residue was dried under high vacuum and dissolved in DMF. After filtration, filtrate was concentrated by evaporation to a small volume and the product was separated by $C_{18}$ reverse phase HPLC using buffer A (1% TFA in water) and buffer B (1% TFA acetonitrile) from 10% buffer B to 70% buffer B to provide a white solid (83%). MS (ESI) 599.18, 597.18 (M+H$^+$).

12. 2-({2-[4-(4-Carbamoyl-4'-chloro-biphen-2-yl-methoxy)-2-fluoro-phenyl]-1-cyclohexyl-1H-benzimidazole-5-carbonyl}-amino)-3-(5-hydroxy-1H-indol-3-yl)-propionic acid hydrochloride (Compound 61)

To a solution of compound 60 (80 mg, 0.134 mmol) in anhydrous DMF (3 mL) in the presence of N,N-diisopropylethylamine (0.1 mL) was added pfp trifluoroacetate (69 μL, 0.408 mmol) at 0° C. The reaction mixture was stirred at room temperature 14 h. After evaporation of solvent, the residue was dissolved EtOAc (30 mL) and the solution was washed with water (10 mL) and dried over anhydrous $Na_2SO_4$. Solvent was evaporated to dryness and residue was then dissolved in anhydrous DMF (5 mL). L-5-Hydroxytryptophan (59 mg, 0.268 mmol) and N,N-diisopropylethylamine (50 μl) was added to above solution. The mixture was stirred at room temperature overnight. Separation of compound by HPLC was according to the procedure for the preparation of compound 60. The product was dissolved in MeOH (2 mL) and 4 N HCl in 1,4-dioxane (0.5 mL) was added at 0° C. The solution was diluted with water (25 mL) and lyophilized to give a pale brown powder (15 mg, 14%).

$^1$H NMR (DMSO-d$_6$) δ 10.48 (1H, d, J=2.4 Hz), 8.80 (1H, d, J=7.5 Hz), 8.27 (1H, d, J=1.2 Hz), 8.16 (1H, d, J=1.8 Hz), 8.11-8.08 (2H, m), 7.97 (1H, dd, J=2.1, 8.4 Hz), 7.88 (1H, d, J=7.2 Hz), 7.63 (1H, t, J=8.7 Hz), 7.52-7.43 (5H, m), 7.17 (1H, dd, J=2.1, 12.0 Hz), 7.10-7.02 (3H, m), 6.88 (1H, d, J=2.4 Hz), 6.57 (1H, dd, J=2.1, 8.4 Hz), 5.12 (2H, s), 4.66-4.62 (1H, m), 4.10-4.00 (1H, m), 3.19 (2H, d, J=4.8 Hz), 2.24-2.20 (2H, m), 1.98-1.86 (4H, m), 1.61 (1H, m), 1.34-1.23 (4H, m). MS (ESI) 802.28, 800.27 (M+H$^+$).

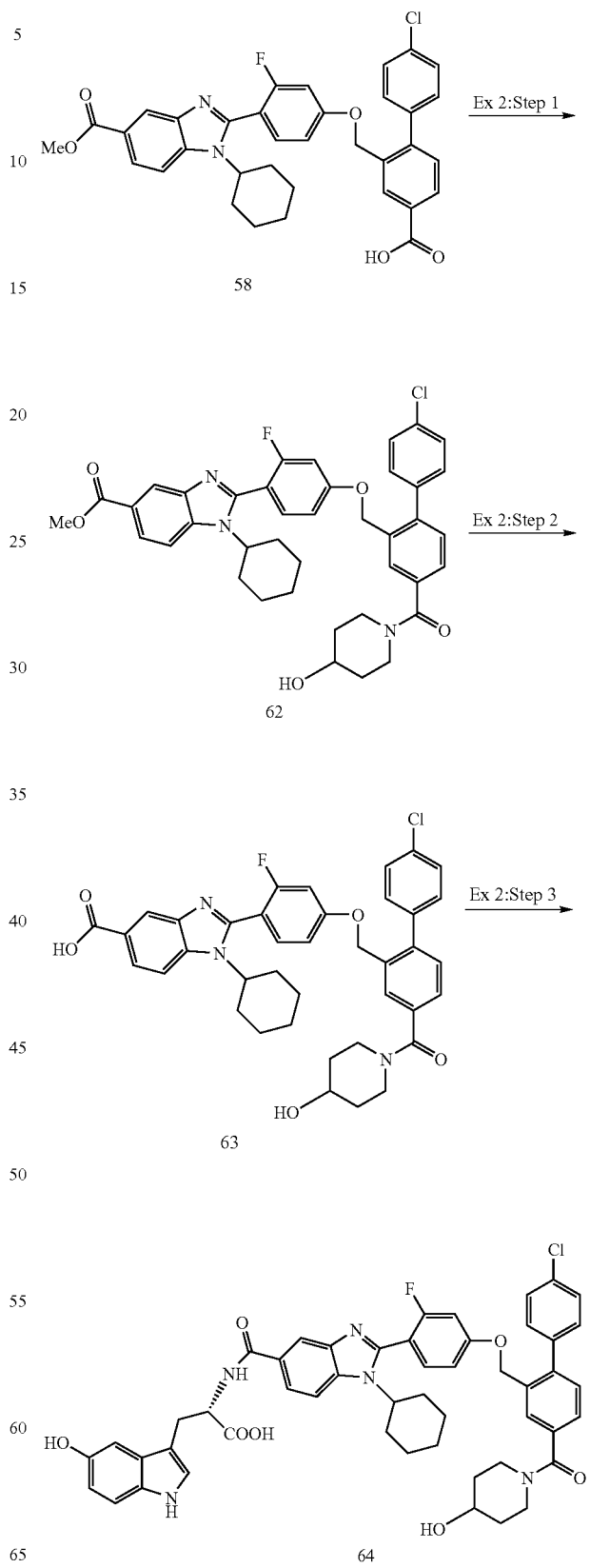

Scheme 5

Example 2

Preparation of 2-[(2-{4-[4'-Chloro 4-(4-hydroxyl-piperidine-1-carbonyl)-biphen-2-ylmethoxy]-2-fluorophenyl}-1-cyclohexyl-1H-benzimidazole-5-carbonyl)-amino]-3-(5-hydroxy-1H-indol-3-yl)-propionic Acid Hydrochloride (Compound 64)

Scheme 2 Above Corresponds to the Following Procedures

1. 2-{4-(4'-Chloro-4-(hydroxyl-piperidine-1-carbonyl)-biphen-2-ylmethoxy)-2-fluoro-phenyl}-1-cyclohexyl-1H-benzimidazole-5-carboxylic acid methyl ester (Compound 62)

Step 1: To a solution of compound 58 (0.21 g, 0.34 mmol) in DMF (10 mL) in the presence of N,N-diisopropylethylamine (0.12 mL) was added pfp trifluoroacetate (0.12 mL, 0.39 mmol) dropwise at 0° C. The reaction was stirred at room temperature for 8 h and evaporated to dryness. The residue was dissolved in EtOAc (80 mL). The solution was washed with water (10 mL×2), dried over anhydrous $Na_2SO_4$, and evaporated.

Step 2: The residue was dissolved anhydrous DMF (8 mL) and 4-hydroxypiperidine (69.3 mg, 0.68 mmol) and N,N-diisopropylethylamine (0.1 mL) were added. The reaction mixture was stirred at room temperature overnight. After evaporation of solvent, the residue was purified by chromatography eluted with $CHCl_3$—MeOH (40:1) to give a pale yellow powder (0.2 g, 84%). MS (ESI) 696.23 (M+H$^+$).

2. 2-{4-(4'-Chloro-4-(hydroxyl-piperidine-1-carbonyl)-biphen-2-ylmethoxy)-2-fluorophenyl}-1-cyclohexyl-1H-benzimidazole-5-carboxylic acid (Compound 63)

Compound 62 (0.18 g, 0.259 mmol) was hydrolyzed to give compound 63 according to the procedure for the preparation of compound 60 in example 1. Yield: 85%. MS (ESI) 684.25, 683.25, 682.25 (M+H$^+$).

3. 2-[(2-{4-[4'-Chloro 4-(4-hydroxyl-piperidine-1-carbonyl)-biphen-2-ylmethoxy]-2-fluorophenyl}-1-cyclohexyl-1H-benzimidazole-5-carbonyl)-amino]-3-(5-hydroxy-1H-indol-3-yl)-propionic acid hydrochloride (Compound 64)

Compound 64 was prepared from compound 63 (90 mg, 0.132 mmol), pfp trifluoroacetate (58 μL, 0.264 mmol), and L-5-hydroxytryptophan (97 mg, 0.44 mmol) according to the procedure for the preparation of compound 61 in example 1. Yield: 46%.

$^1$H NMR (DMSO-d$_6$) δ 10.48 (1H, s), 8.77 (1H, d, J=6.9 Hz), 8.26 (1H, s), 8.06 (1H, d, J=9.0 Hz), 7.86 (1H, d, J=7.4 Hz), 7.86 (1H, d, J=8.4 Hz), 7.66 (1H, s), 7.60 (1H, t, J=8.4 Hz), 7.48-7.39 (5H, m), 7.17-7.07 (3H, m), 7.01 (1H, d, J=8.7 Hz), 6.88 (1H, d, J=2.1 Hz), 6.56 (1H, dd, J=2.1, 8.4 Hz), 5.13 (2H, s), 4.65-4.63 (1H, m), 4.04-4.00 (1H, m), 3.77-3.64 (4H, m), 3.23-3.15 (4H, m), 2.23-2.20 (2H, m), 1.85-1.61 (6H, m), 1.33-1.18 (6H, m).MS (ESI) 886.33, 885.34, 884.33 (M+H$^+$).

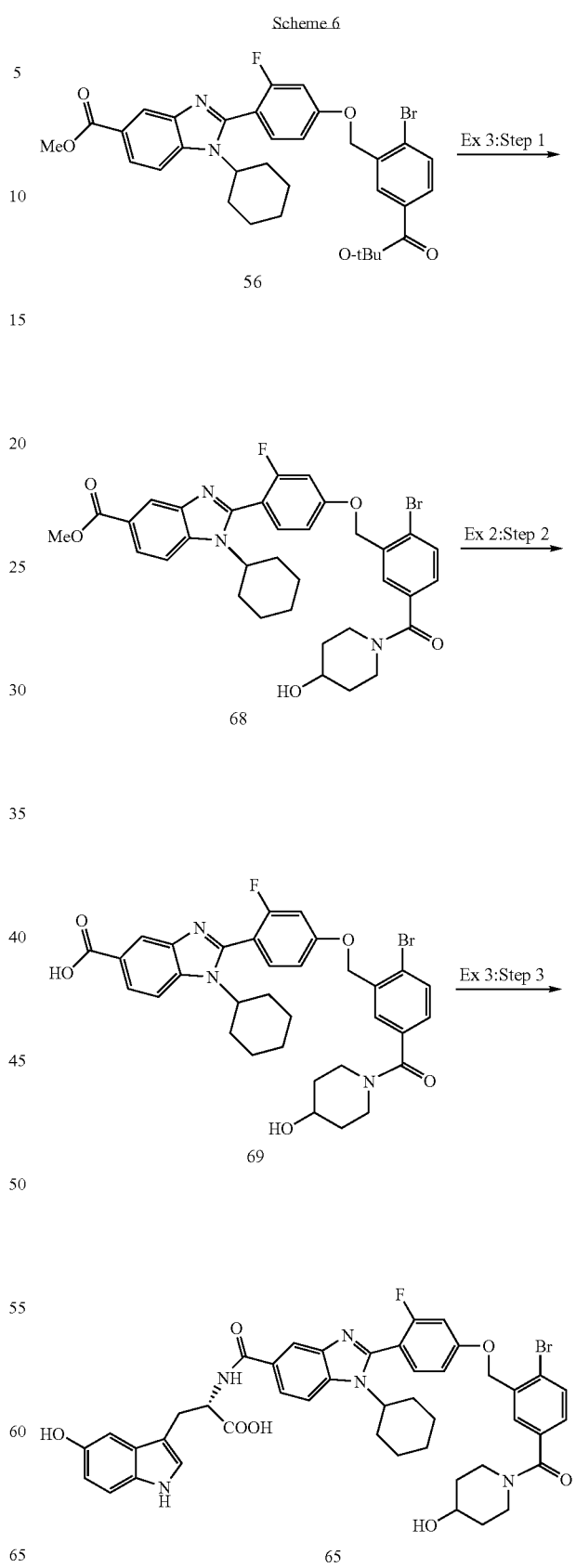

Scheme 6

Example 3

Preparation of 2-[(2-{4-[2-Bromo-5-(4-hydroxyl-piperidine-1-carbonyl)-benzyloxy]-2-fluoro-phenyl}-1-cyclohexyl-1H-benzimidazole-5-carbonyl)-amino]-3-(5-hydroxy-1H-indol-3-yl)-propionic acid hydrochloride (Compound 65)

Scheme 6 Above Corresponds to the Following Procedures

1. 2-{4-[2-Bromo-5-(4-hydroxy-piperidine-1-carbonyl)-benzyloxy]-2-fluoro-phenyl}-1-cyclohexyl-1H-benzimidazole-5-carboxylic acid methyl ester (Compound 68)

Compound 56 (0.308 g, 0.483 mmol) was dissolved in anhydrous dichloromethane (3 mL) and TFA (3 mL) was added. The mixture was stirred at room temperature for 1 h. After evaporation of solvent, the residue was dissolved in dichloromethane (3 mL) and DMF (3 mL).

To the above solution was added N,N-diisopropylethylamine (0.4 mL) followed by addition of pfp trifluoroacetate (0.4 mL) at 0° C. The reaction was stirred at room temperature for 6 h and worked up according the procedure for preparation of compound 62 step 2 in example 2.

Above residue was reacted with 4-hydroxypiperidine (97.7 mg, 0.996 mmol) in anhydrous DMF (5 mL) in the presence of N,N-diisopropylethylamine (0.1 mL) according to the procedure for the preparation of compound 62. It gave a pale foam (0.31 g, 97%). MS (ESI) 666.15, 664.15 (M+H$^+$).

2. 2-{4-[2-Bromo-5-(4-hydroxy-piperidine-1-carbonyl)-benzyloxy]-2-fluoro-phenyl}-1-cyclohexyl-1H-benzimidazole-5-carboxylic Acid (Compound 69)

This compound was prepared according to the procedure for the preparation of compound 60 in example 1. Yield 95%. MS (ESI) 652.16, 650.17 (M+H$^+$).

3. 2-[(2-{4-[2-Bromo-5-(4-hydroxyl-piperidine-1-carbonyl)-benzyloxy]-2-fluoro-phenyl}-1-cyclohexyl-1H-benzimidazole-5-carbonyl)-amino]-3-(5-hydroxy-1H-indol-3-yl)-propionic acid hydrochloride (Compound 65)

Compound 69 (0.17 g, 0.261 mmol) was treated with pfp trifluoroacetate (90 µL, 0.522) in anhydrous DMF (8 mL) in the presence of N,N-diisopropylethylamine (90 µl) followed by reaction with L-5-hydroxytryptophan (0.115 g, 0.522 mmol) according to the procedure for the preparation of compound 64 in example 2 to give compound 65 (0.116 g, 74%). MS (ESI) 855.25, 854.25, 852.25 (M+H$^+$).

$^1$H NMR (DMSO-d$_6$) δ 10.48 (1H, s), 8.77 (1H, d, J=7.2 Hz), 8.27 (1H, s), 8.08 (1H, d, J=7.6 Hz), 7.87 (1H, d, J=7.4 Hz), 7.76 (1H, d, J=8.0 Hz), 7.66-7.62 (3H, m), 7.35-7.27 (2H, m), 7.18 (1H, dd, J=1.4, 7.6 Hz), 7.08-7.02 (3H, m), 6.85 (1H, s), 6.54 (1H, d, J=8.2 Hz), 5.25 (2H, s), 4.62 (1H, m), 4.08 (1H, m), 3.76-3.62 (4H, m), 3.42 (1H, m), 3.20-3.03 (4H, m), 2.21-2.08 (2H, m), 1.84-1.58 (6H, m), 1.32-1.21 (4H, m).

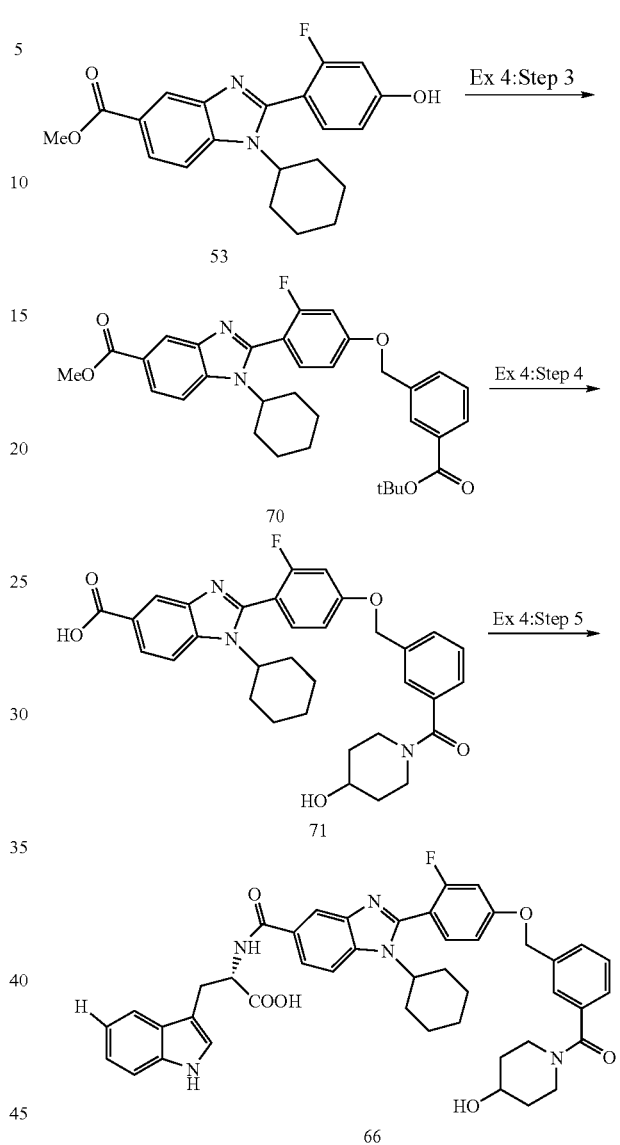

Example 4

Preparation of 2-[(1-Cyclohexyl-2-{2-fluoro-4-[3-(4-hydroxyl-piperidine-1-carbonyl)-benzyloxy]-phenyl}-1H-benzimidazole-5-carbonyl)-amino]-3-(5-hydroxy-1H-indol-3-yl)-propionic acid hydrochloride (Compound 66)

Scheme 7 Above Corresponds to the Following Procedures

1. 3-Methyl-benzoic acid tert-butyl ester

4-Bromo-3-methyl-benzoic acid tert-butyl ester (0.39 g, 1.438 mmol) was hydrogenated over 10% Pd—C (0.5 g) under H$_2$ (50 psi) in EtOAc—MeOH (4:1, 20 mL) for 5 h. After filtration through Celite, filtrate was evaporated to dryness. Yield: 97%. MS (ESI) 193.28 (M+H$^+$).

2. 3-Bromomethyl-benzoic acid tert-butyl ester

The crude 3-methyl-benzoic acid tert-butyl ester was reacted with NBS (0.31 g, 1.726 mmol), AIBN (0.28 g, 1.726 mmol) in CCl$_4$ (30 mL) according to the procedure for the preparation of compound 55 in example 1. After separation by chromatography eluted with CHCl$_3$—MeOH (50:1), a mixture of two products was obtained. One of them was the product (61% pure) with MS (ESI) 272.76 (M+H$^+$). This mixture was not further separated and directly used in the next step reaction.

3. 2-[4-(3-tert-Butoxycarbonyl-benzyloxy)-2-fluoro-phenyl]-1-cyclohexyl-1H-benzimidazole-5-carboxylic acid methyl ester (Compound 70)

Compound 53 (0.242 g, 0.656 mmol) was reacted with crude 3-bromomethyl-benzoic acid tert-butyl ester (0.178 g) in the presence of K$_2$CO$_3$ (0.18 g) in DMF (8 mL) according to the procedure for the preparation of compound 56 in example 1. The purification by chromatography eluted with CHCl$_3$—MeOH (55:1) gave compound 70 (0.118 g). MS (ESI) 559.23 (M+H$^+$).

4. 1-Cyclohexyl-2-{2-fluoro-4-[3-(4-hydroxy-piperidine-1-carbonyl)-benzyloxy]-phenyl}-1H-benzimidazole-5-carboxylic acid (Compound 71)

Compound 71 was prepared from compound 70 (0.115 g, 0.206 mmol) and 4-hydroxypiperidine (41 mg, 0.412 mmol) according to the procedure for the preparation of compound 62 in example 2. The product was used for the next step reaction without further purification.

Above crude product was hydrolyzed according to the produce for the preparation of compound 60 in example 1. It gave a solid (96.1 mg, 80%). MS (ESI) 572.27 (M+H$^+$).

5. 2-[(1-Cyclohexyl-2-{2-fluoro-4-[3-(4-hydroxyl-piperidine-1-carbonyl)-benzyloxy]-phenyl}-1H-benzimidazole-5-carbonyl)-amino]-3-(5-hydroxy-1H-indol-3-yl)-propionic acid hydrochloride (Compound 66)

Compound 66 was prepared from compound 71 (70 mg, 0.122 mmol) and L-5-hydroxytryptophan (54 mg, 0.244 mmol) according to the procedure for the preparation of compound 61 in example 1. Yield: 64%.

$^1$H NMR (DMSO-d$_6$) δ 10.49 (1H, s), 8.78 (1H, d, J=6.0 Hz), 8.26 (1H, s), 8.07 (1H, d, J=7.8 Hz), 7.86 (1H, d, J=6.9 Hz), 7.64-7.48 (3H, m), 7.34 (1H, d, J=6.9 Hz), 7.26 (1H, d, J=12.3 Hz), 7.14-7.07 (3H, m), 6.88 (1H, s), 6.56 (1H, d, J=8.1 Hz), 5.29 (2H, s), 4.64 (1H, m), 4.09 (1H, m), 3.46 (1H, m), 3.19-3.08 (4H, m), 2.23-2.20 (2H, m), 1.85-1.58 (6H, m), 1.30-1.26 (8H, m). MS (ESI) 774.32 (M+H$^+$).

Scheme 8

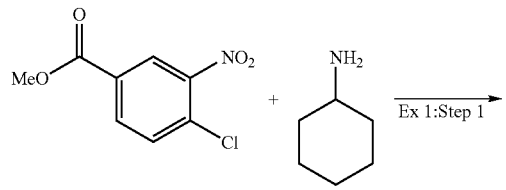

-continued

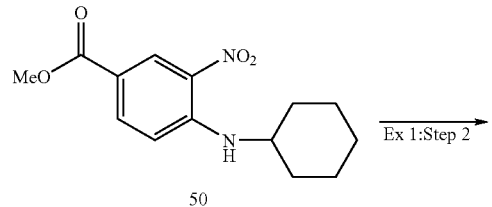

50

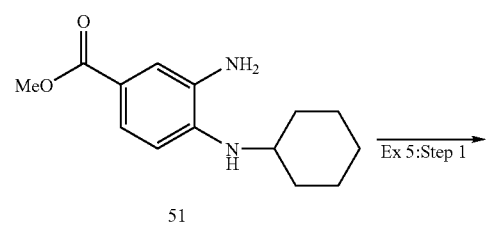

51

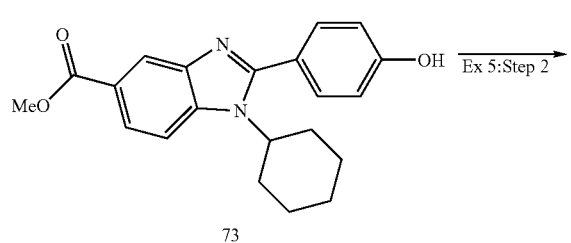

73

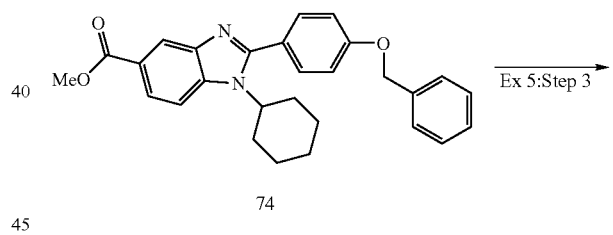

74

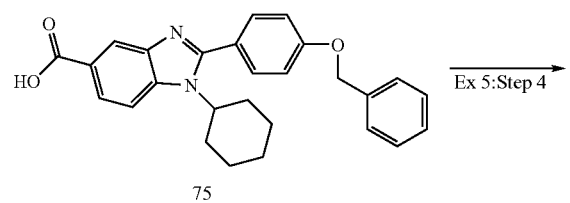

75

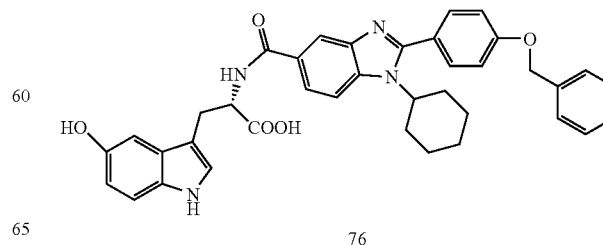

76

Example 5

Preparation of 2-{[2-(4-Benzyloxy-phenyl)-1-cyclo-hexyl-1H-benzimidazole-5-carbonyl]-amino}-3-(5-hydroxy-1H-indol-3-yl)-propinic acid hydrochloride (Compound 76)

Scheme 8 Above Corresponds to the Following Procedures 1. 1-Cyclohexyl-2-(4-hydroxyphenyl)-1H-benzimidazole-5-carboxylic acid methyl ester (Compound 73)

Compound 51 (3 g, 12.08 mmol) was dissolved in DMF (15 mL) and water (0.5 mL). 4-Hydroxybenzaldehyde (1.844 g, 15.1 mmol) was added followed by addition of Oxone® (4.827 g, 7.85 mmol). The mixture was stirred at room temperature for 1 h and water (6 mL) was then added.

3. 2-(4-Benzyloxy-phenyl)-1-cyclohexyl-1H-benzimidazole-5-carboxylic acid (Compound 75)

Compound 75 was prepared from compound 74 (0.428 g, 0.971 mmol) according to the procedure for the preparation of compound 60 in example 1. Yield: 99%. MS (ESI) 447.21 (M+H$^+$).

4. 2-{[2-(4-Benzyloxy-phenyl)-1-cyclohexyl-1H-benzimidazole-5-carbonyl]-amino}-3-(5-hydroxy-1H-indol-3-yl)-propinic acid hydrochloride (Compound 76)

Compound 76 was prepared from compound 71 (0.1 g, 0.234 mmol) and L-5-hydroxytryptophan (0.103 g, 0.468 mmol) according to the procedure for the preparation of compound 61 in example 1. Yield: 82%.

$^1$H NMR (DMSO-d$_6$) δ 10.54 (1H, d, J=2.1 Hz), 9.02 (1H, d, J=7.5 Hz), 8.31 (1H, d, J=1.2 Hz), 8.27 (1H, d, J=9.0 Hz), 8.00 (1H, dd, J=1.2, 8.7 Hz), 7.76 (2H, d, J=9.0 Hz), 7.51-7.33 (7H, m), 7.11-7.07 (2H, m), 6.89 (1H, d, J=2.1 Hz), 6.58 (1H, dd, J=1.8, 8.7 Hz), 5.26 (2H, s), 4.69-4.61 (1H, m), 4.36 (1H, t), 3.21(2H, d, J=3.9 Hz), 2.36-2.22 (2H, m), 2.06 (2H, br s), 1.87-1.84 (2H, m), 1.65-1.23 (4H, m).MS (ESI) 629.21 (M+H$^+$).

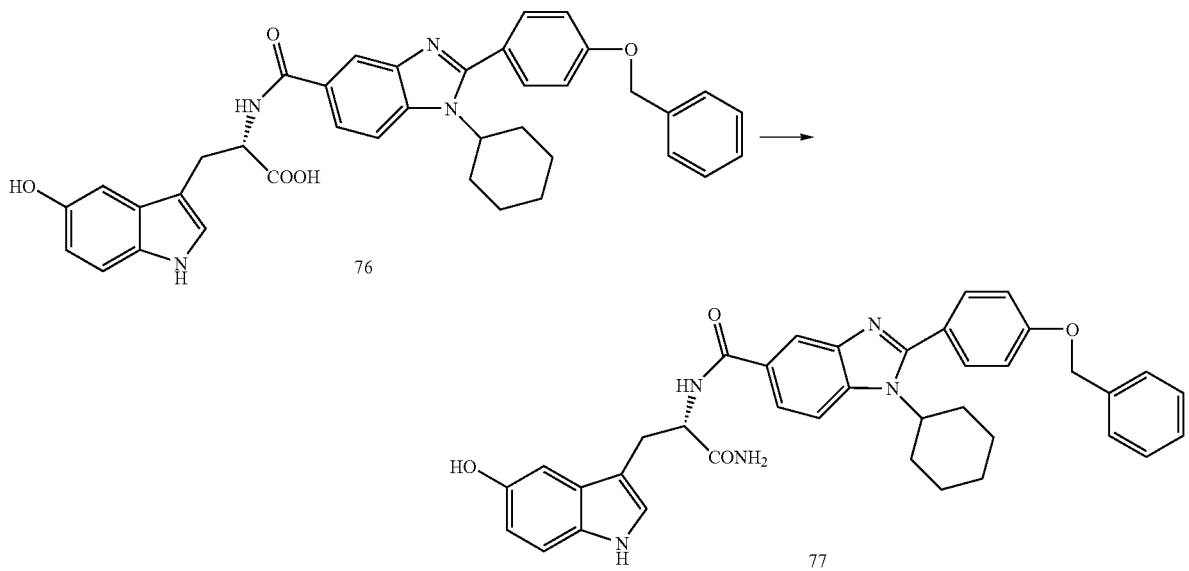

Scheme 9

The suspension was neutralized to pH 9 with 2 N aq. NaOH at 0° C. The precipitate was collected by filtration, washed with water and dried to give a gray powder (3.4 g, 81%). MS (ESI): 351.17 (M+H$^+$).

2. 2-(4-Benzyloxy-phenyl)-1-cyclohexyl-1H-benzimidazole-5-carboxylic acid methyl ester (Compound 74)

Compound 74 was prepared from compound 73 (0.6 g, 1.71 mmol) and benzyl bromide (0.407 mL, 3.42 mmol) in the presence of K$_2$CO$_3$ (0.47 g) in DMF (20 mL) according to the procedure for the preparation of compound 56 in example 1. Yield: 96%. MS (ESI) 441.25 (M+H$^+$).

Example 6

Preparation of 2-(4-Benzyloxy-phenyl)-1-cyclohexyl-1H-benzimidazole-5-carboxylic acid [1-carbamoyl-2-(5-hydroxy-1H-indol-3-yl)-ethyl]-amide Hydrochloride (Compound 77)

Scheme 9 Above Corresponds to the Following Procedure

Compound 77 was prepared from compound 76 (0.1 g) according to the procedure for the preparation of compound 59 in example 1. Yield: 74%.

$^1$H NMR (DMSO-d$_6$) δ 11.77 (2H, br s), 10.43 (1H, d, J=2.1 Hz), 8.80 (1H, d, J=7.8 Hz), 8.29 (1H, s), 8.25 (1H, d, J=8.7 Hz), 8.00 (1H, d, J=7.4 Hz), 7.86 (1H, d, J=8.7 Hz), 7.75 (2H, d, J=8.4 Hz), 7.64 (1H, s), 7.50-7.32 (6H, m), 7.10-7.04 (2H, m), 7.97 (1H, d, J=2.4 Hz), 6.56 (1H, dd,

J=2.4, 8.4 Hz), 6.56 (1H, dd, J=2.1, 8.4 Hz), 5.26 (2H, s), 4.70-4.67 (1H, m), 4.35 (1H, t), 3.19 (2H, d, J=4.1 Hz), 2.30-2.27 (2H, m), 2.04 (2H, br s), 1.87-1.83 (2H, m), 1.61-1.18 (4H, m). MS (ESI) 628.29 (M+H$^+$).

1.14 mmol) in the presence of K$_2$CO$_3$ (0.158 g) in DMF (8 mL) according to the procedure for the preparation of compound 56 in example 1. Yield: 94%. MS (ESI) 491.26 (M+H$^+$).

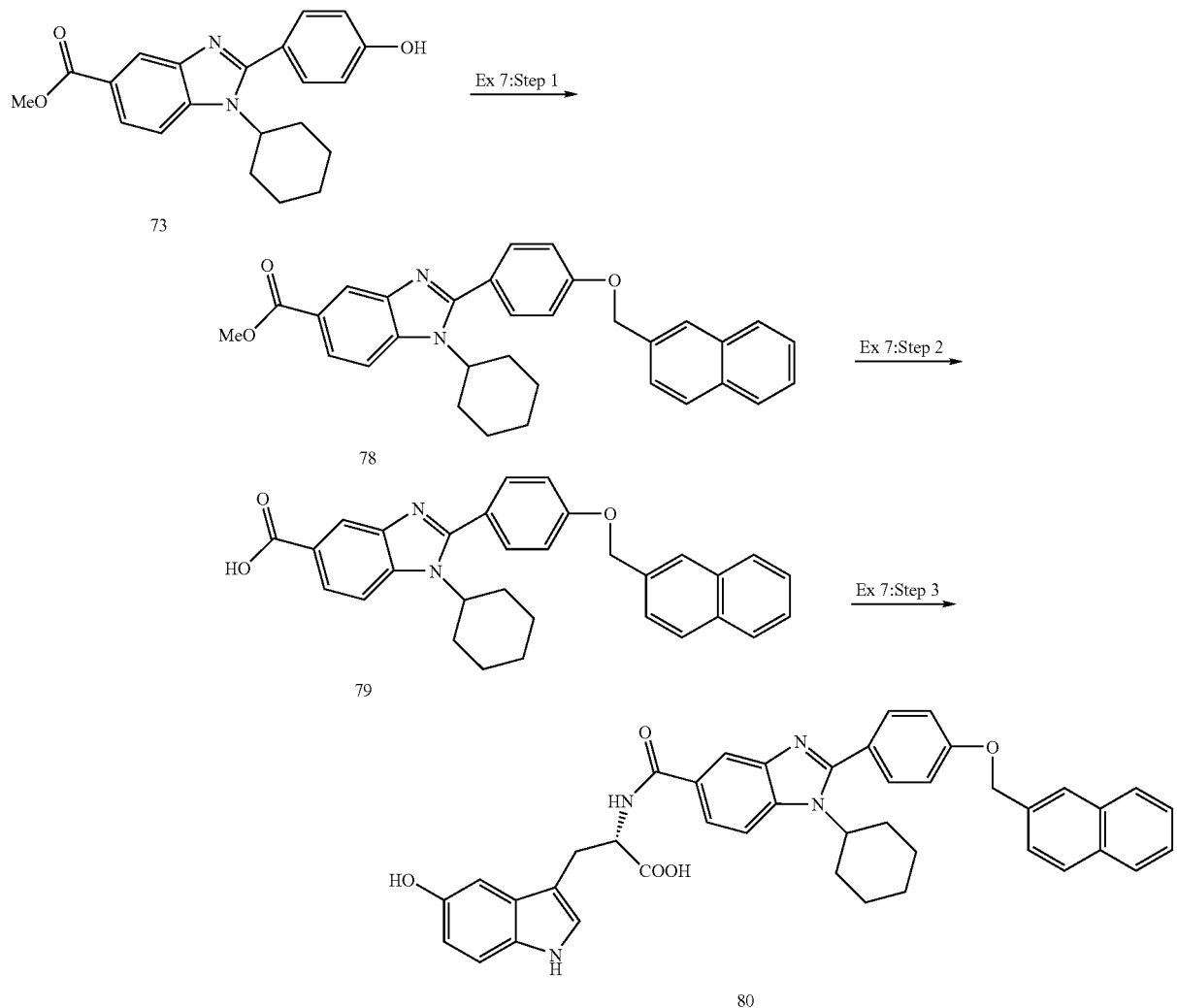

Scheme 10

Example 7

Preparation of 2-({1-Cyclohexyl-2-[4-(naphthalene-2-ylmethoxy)-phenyl]-1H-benzimidazole-5-carbonyl}-amino)-3-(5-hydroxy-1H-indol-3-yl)-propinic acid hydrochloride (Compound 80)

Scheme 10 Above Corresponds to the Following Procedures 1. 1-Cyclohexyl-2-[4-(naphthalen-2ylmethoxy)-phenyl]-1H-benzimidazole-5-carboxylic acid methyl ester (Compound 78)

Compound 78 was prepared from compound 73 (0.2 g, 0.57 mmol) with 2-(bromomethyl)naphthalene (0.252 g, 2. 1-Cyclohexyl-2-[4-(naphthalen-2ylmethoxy)-phenyl]-1H-benzoimidazole-5-carboxylic acid (Compound 79)

Compound 79 was prepared from compound 78 (0.108 g, 0.22 mmol) according to the procedure for the preparation of compound 60 in example 1. Yield: 96%. MS (ESI) 477.24 (M+H$^+$).

3. 2-({1-Cyclohexyl-2-[4-(naphthalene-2-yl-methoxy)-phenyl]-1H-benzimidazole-5-carbonyl}-amino)-3-(5-hydroxy-1H-indol-3-yl)-propinic acid hydrochloride (Compound 80)

Compound 80 was prepared from compound 79 (90 mg, 0.189 mmol) and L-5-hydroxytryptophan (83 mg, 0.378 mmol) according to the procedure for the preparation of compound 61 in example 1. Yield: 80%.

$^1$H NMR (DMSO-d$_6$) δ 10.54 (1H, d, J=1.8 Hz), 8.31 (1H, s), 8.30 (1H, d, J=8.7 Hz), 8.04 (1H, s), 8.02 (1H, dd, J=1.2, 9.0 Hz), 7.98-7.92 (3H, m), 7.78 (2H, d, J=8.7 Hz), 7.62

(1H, dd, J=1.5, 8.4 Hz), 7.55-7.51 (2H, m), 7.41 (2H,d,J=8.7 Hz), 7.10 (1H, s), 7.08 (1H, d, J=6.0 Hz), 6.89 (1H, d, J=1.8 Hz), 6.57 (1H, dd, J=2.1, 8.7 Hz), 5.44 (2H, s), 4.69-4.62 (1H, m), 4.37 (1H, t), 3.21 (2H, d, J=3.6 Hz), 2.41-2.23 (2H, m), 2.06 (2H, br s), 1.87-1.83 (2H, m), 1.46-1.22 (4H, m). MS (ESI) 679.31 (M+H$^+$).
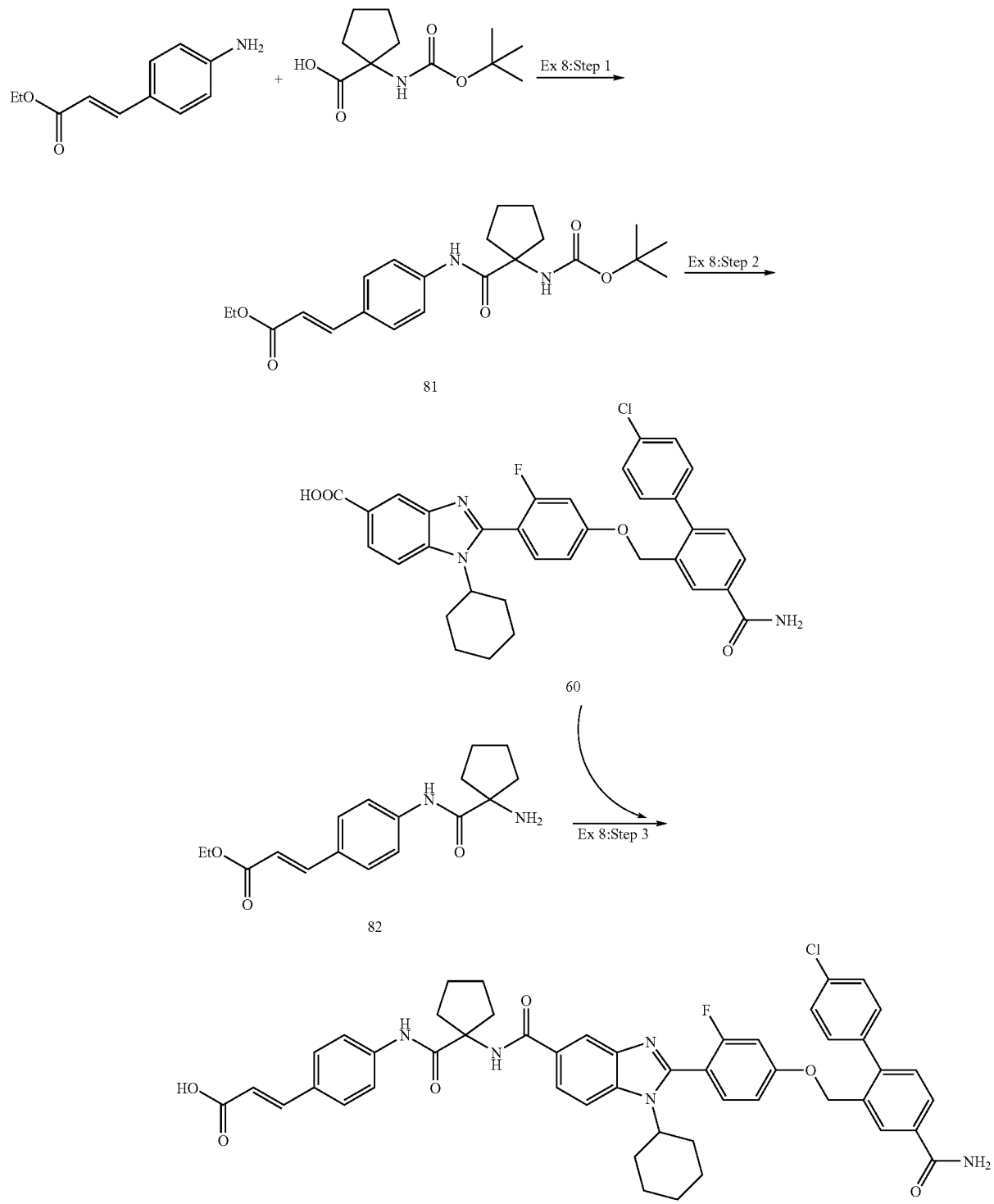

Example 8

Preparation of 3-(4-{[1-({2-[4-(4-Carbamoyl-4'-chloro-biphen-2-ylmethoxy)-2-fluoro-phenyl]-1-cyclohexyl-1H-benzoimidazole-5-carbonyl}-amino)-cyclopentanecarbonyl]-amino}-phenyl)-acrylic acid (Compound 83)

Scheme 11 Above Corresponds to the Following Procedures

1. 3-{4-[(1-tert-Butoxycarbonylamino-cyclopentanecarbonyl)-amino]-phenyl}-acrylic acid ethyl ester (Compound 81)

A mixture of 1-tert-butoxycarbonylamino-cyclopentanecarboxylic acid (1 g, 4.36 mmol), HATU (1.22 g, 4.36 mmol) and DIEA (1.52 mL, 8.72 mmol) in anhydrous DMF (10 mL) was stirred at room temperature for 30 min. 3-(4-Aminophenyl)-acrylic acid ethyl ester (1 g, 5.23 mmol) was added. The reaction mixture was stirred at room temperature for 4 days. Precipitates formed was collected by filtration and washed with ether to give compound 81 (42%). MS (ESI) 403.25 (M+H$^+$).

2. 3-{4-[(1-Amino-cyclopentanecarbonyl)-amino]-phenyl}-acrylic acid ethyl ester (Compound 82)

To compound 81 (300 mg) was added 4 N HCl in dioxane (5 mL) and the reaction mixture was stirred at room temperature overnight. After removal of solvent, compound 82 was afforded. Yield 100%. MS (ESI) 303.16 (M+H$^+$).

3. 3-(4-{[1-({2-[4-(4-Carbamoyl-4'-chloro-biphen-2-ylmethoxy)-2-fluoro-phenyl]-1-cyclohexyl-1H-benzoimidazole-5-carbonyl}-amino)-cyclopentanecarbonyl]-amino}-phenyl)-acrylic acid (Compound 83)

To a solution of compound 60 (50 mg, 0.0836 mmol) in anhydrous DMF (3 mL) in the presence of DIEA (36.4 µL, 0.21 mmol) was added HBTU (36.4 mg, 0.096 mmol). The mixture was stirred at room temperature for 30 min. Compound 82 (36.4 mg, 0.0878 mmol) was added and the reaction mixture was stirred at room temperature overnight. After removal of solvent, the residue was dissolved in MeOH (2 mL) and 2 N aqueous NaOH (1 mL) was added. The mixture was stirred at 45° C. for 2 h and cooled in an ice-bath. The reaction solution was neutralized with 4 N HCl to pH 3. After removal of solvent, the residue was dried and dissolved in a small amount of MeOH and filtered off precipitates. Purification by C$_{18}$ reverse phase HPLC and formation of HCl salt were according to the procedure of the preparation of compound 61. Yield 64%.

$^1$H NMR (DMSO-d$_6$) δ 9.72 (1H, s), 8.61 (1H, s), 8.43 (1H, s), 8.16 (1H, d, J=1.8 Hz), 8.10 (1H, s), 8.03 (1H, d, J=8.7 Hz), 7.97 (1H, dd, J=1.8, 8.1 Hz), 7.90 (1H, d, J=8.4 Hz), 7.65-7.43 (9H, m), 7.15 (1H, dd, J=2.1, 12.0 Hz), 7.02 (1H, dd, J=2.1, 8.7 Hz), 6.30 (1H, d, J=16 Hz), 5.12 (2H, s), 4.06 (1H, m), 2.33-2.08 (6H, m), 1.86-1.67 (8H, m), 1.34-1.23 (4H, m). MS(ESI) 852.26, 853.25, 854.24 (M−H$^+$).

BIOLOGICAL EXAMPLES

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73: 1649-1654, 1999; Ishii et al., *Hepatology*, 29: 1227-1235, 1999; Lohmann et al., *Jnl of Bio. Chem.*, 274: 10807-10815, 1999; and Yamashita et al., *Jnl. of Bio. Chem.*, 273: 15479-15486, 1998.

WO 97/12033, filed on Sep. 27, 1996, by Emory University, listing C. Hagedorn and A. Reinoldus as inventors, which claims priority to U.S. Ser. No. 60/004,383, filed on September, 1995, describes an HCV polymerase assay that can be used to evaluate the activity of the of the compounds described herein. Another HCV polymerase assay has been reported by Bartholomeusz, et. al., Hepatitis C Virus (HCV) RNA polymerase assay using cloned HCV non-structural proteins; Antiviral Therapy 1996: 1 (Supp 4) 18-24.

Screens that measure reductions in kinase activity from HCV drugs are disclosed in U.S. Pat. No. 6,030,785, to Katze et al., U.S. patent No. Delvecchio et al., and U.S. Pat. No. 5,759,795 to Jubin et al. Screens that measure the protease inhibiting activity of proposed HCV drugs are disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) is used for screening of compounds of the present invention for HCV RNA dependent RNA polymerase. The ET cell line is stably transfected with RNA transcripts harboring a I$_{389}$luc-ubineo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T12801; K1846T) (Krieger at al, 2001 and unpublished). The ET cells are grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They are all available through Life Technologies (Bethesda, Md.). The cells are plated at 0.5-1.0×10$^4$ cells/well in the 96 well plates and incubated for 24 h before adding nucleoside analogs. Then the compounds each at 5 and 50 µM will be added to the cells. Luciferase activity will be measured 48-72 hours later by adding a lysis buffer and the substrate (Catalog number Glo-lysis buffer E2661 and Bright-Glo leuciferase system E2620 Promega, Madison, Wis.). Cells should not be too confluent during the assay. Percent inhibition of replication will be plotted relative to no compound control. Under the same condition, cytotoxicity of the compounds will be determined using cell proliferation reagent, WST-1 (Roche, Germany). The compounds showing antiviral activities, but no significant cytotoxicities will be chosen to determine IC$_{50}$ and TC$_{50}$.

Example 3

Cloning and Expression of Recombinant HCV-NS5b

The coding sequence of NS5b protein is cloned by PCR from $pFKI_{389}luc/NS3-3'/ET$ as described by Lohmann, V., et al. (1999) *Science* 285, 110-113 using the following primers:

```
                                           (SEQ. ID. NO. 1)
        aggacatggatccgcggggtcgggcacgagacag (SEQ. ID. NO. 2)
        aaggctggcatgcactcaatgtcctacacatggac
```

The cloned fragment is missing the C terminus 21 amino acid residues. The cloned fragment is inserted into an IPTG-inducible expression plasmid that provides an epitope tag (His)6 at the carboxy terminus of the protein.

The recombinant enzyme is expressed in XL-1 cells and after induction of expression, the protein is purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a biotinylated, heteropolymeric template, which includes a portion of the HCV genome. Typically, the assay mixture (50 uL) contains 10 mM Tris-HCl (pH 7.5), 5 mM $MgCl_2$, 0.2 mM EDTA, 10 mM KCl, 1 unit/uL RNAsin, 1 mM DTT, 10 uM each of NTP, including $[^3H]$-UTP, and 10 ng/uL heteropolymeric template. Test compounds are initially dissolved in 100% DMSO and further diluted in aqueous buffer containing 5% DMSO. Typically, compounds are tested at concentrations between 1 nM and 100 uM. Reactions are started with addition of enzyme and allowed to continue at 37° C. for 2 hours. Reactions are quenched with 8 uL of 100 mM EDTA and reaction mixtures (30 uL) are transferred to streptavidin-coated scintillation proximity microtiter plates (FlashPlates) and incubated at 4° C. overnight. Incorporation of radioactivity is determined by scintillation counting.

FORMULATION EXAMPLES

The following are representative pharmaceutical formulations containing a compound of formula I, Ia, Ib, II, III or IV.

Example 1

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Amount |
| --- | --- |
| compound of this invention | 0.2 mg-20 mg |
| sodium acetate buffer solution, 0.4 M | 2.0 mL |
| HCl (1 N) or NaOH (1 N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| Compound of the invention | 500 mg |
| Witepsol ® H-15 | balance |

---

---

What is claimed is:

1. A compound of the formula I:

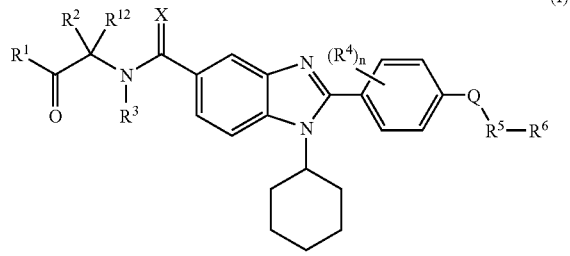

wherein:

$R^1$ is selected from the group consisting of —$OR^7$, and —$NR^8R^9$;

where $R^7$ is selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic;

$R^8$ and $R^9$ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, $R^8$ and $R^9$, together with the nitrogen atom pendent thereto, form a heterocyclic or substituted heterocyclic ring group;

$R^2$ and $R^{12}$ are independently selected from the group consisting of hydrogen, alkyl, substituted alkyl, cycloalkyl, substituted cycloalkyl, alkenyl, substituted alkenyl, alkynyl, substituted alkynyl, heterocyclic, and substituted heterocyclic; or, $R^2$ and $R^{12}$, together with the carbon atom pendent thereto, form a cycloalkyl, substituted cycloalkyl, heterocyclic or substituted heterocyclic ring group;

$R^3$ is selected from the group consisting of hydrogen and alkyl; or $R^2$ and $R^3$, together with the nitrogen atom pendent to $R^3$, form a heterocyclic or substituted heterocyclic ring group;

each $R^4$ is selected from the group consisting of halo, nitro, amino, substituted amino, cyano and hydroxyl;

Q is selected from the group consisting of oxygen, —$S(O)_q$— where q is zero, one or two and —$N(R^3)$— where $R^3$ is as defined above;

X is selected from the group consisting of oxygen, sulfur, and =$NR^{11}$, where $R^{11}$ is hydrogen or alkyl:

$R^5$ is alkylene or substituted alkylene;

$R^6$ is selected from the group consisting of substituted aryl, and substituted heteroaryl;

n is 0 to 3;

or pharmaceutically acceptable salts thereof.

2. A compound according to claim 1 wherein said compound is represented by the Formula Ia:

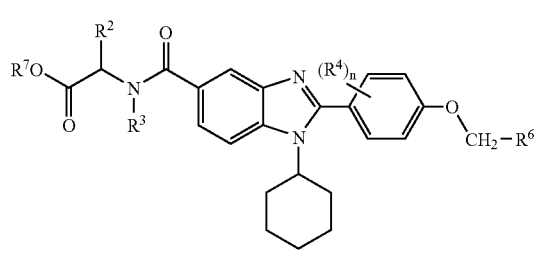

(Ia)

or a pharmaceutically acceptable salt thereof, wherein
- $R^7$ is selected from the group, consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic;
- $R^2$ is substituted or $R^2$ $R^3$, together with the nitrogen pendent $R^3$, form a heterocyclic or substituted heterocyclic ring group;
- $R^3$ is selected from the group consisting of hydrogen and alkyl; or $R^2$ and $R^3$, together with the nitrogen atom pendent to $R^3$, form a heterocyclic or substituted heterocyclic ring group;
- each $R^4$ is selected from the group consisting of halo, nitro, amino, substituted amino, cyano and hydroxyl;
- $R^6$ is selected from the group consisting of substituted aryl, and substituted heteroaryl;
- n is 0 to 3.

3. A compound according to claim 1 wherein said compound is represented by the Formula Ib:

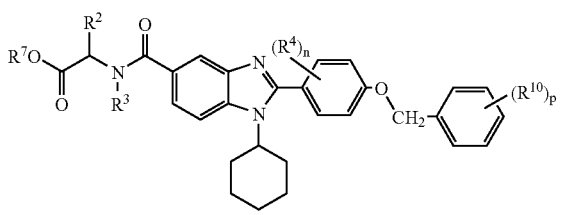

(Ib)

or a pharmaceutically acceptable salt thereof, wherein:
- $R^7$ is selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic;
- $R^2$ is substituted alkyl;
- $R^3$ is selected from the group consisting of hydrogen and alkyl; or $R^2$ and $R^3$, together with the nitrogen atom pendent to $R^3$, form a heterocyclic or substituted heterocyclic ring group;
- each $R^4$ is selected from the group consisting of halo, nitro, amino, substituted amino, cyano and hydroxyl;
- p is 1 to 5;
- each $R^{10}$ is independently selected from the group consisting of alkyl, substituted alkyl, aryl, substituted aryl, heteroaryl, substituted heteroaryl, carboxyl, carboxyl ester, and —C(O)NR$^8$R$^9$ where $R^8$ and $R^9$ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, $R^8$ and $R^9$, together with the nitrogen atom pendent thereto, form a heterocyclic or substituted heterocyclic ring group.

4. A compound according to claim 1 wherein said compound is represented by Formula II:

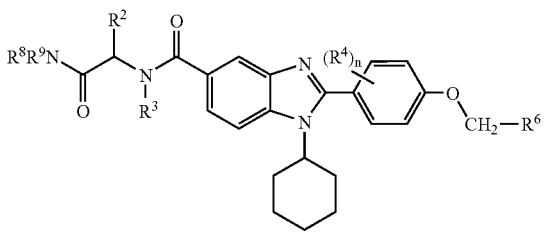

(II)

or a pharmaceutically acceptable salt thereof; wherein:
- $R^2$ is substituted alkyl, or $R^2$ and $R^3$, together with the nitrogen atom pendent to $R^3$, form a heterocyclic or substituted heterocyclic ring group;
- $R^3$ is selected from the group consisting of hydrogen and alkyl; or $R^2$ and $R^3$, together with the nitrogen atom pendent to $R^3$, form a heterocyclic or substituted heterocyclic ring group;
- each $R^4$ is selected from the group consisting of halo, nitro, amino, substituted amino, cyano and hydroxyl;
- $R^6$ is selected from the group consisting of substituted aryl and substituted heteroaryl;
- $R^8$ and $R^9$ independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, $R^8$ and $R^9$, together with the nitrogen atom pendent thereto, form a heterocyclic or substituted heterocyclic ring group.

5. A compound according to claim 1 wherein said compound is represented by Formula III:

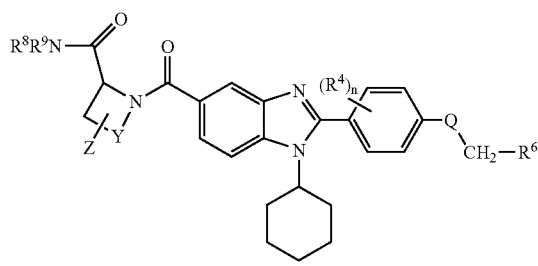

(III)

or a pharmaceutically acceptable salt thereof; wherein:
- each $R^4$ is selected from the group consisting of halo, nitro, amino, substituted amino, cyano and hydroxyl;

R⁶ is selected from the group consisting of substituted aryl, and substituted heteroaryl;

R⁸ and R⁹ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, R⁸ and R⁹, together with the nitrogen atom pendent thereto, form a heterocyclic or substituted heterocyclic ring group;

n is 0 to 3;

Z is selected from the group consisting of hydrogen, hydroxy, halo, alkyl, and aryl; and Y together with the nitrogen and carbon atoms bound thereto form an azetidinyl, pyrrolidinyl, piperadinyl, morpholino, thiomorpholino or piperidinyl.

6. A compound according to claim 1 wherein said compound is represented by Formula IV:

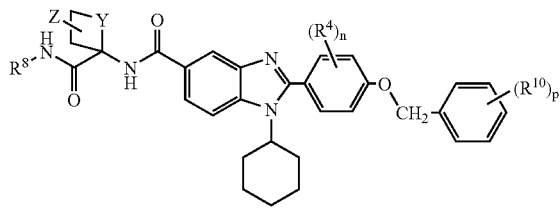

(IV)

wherein each R⁴ is selected from the group consisting of halo, nitro, amino, substituted amino, cyano and hydroxyl;

n is 0 to 3;

R⁸ is selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic;

Z is selected from the group consisting of hydrogen, hydroxy, halo, alkyl, and aryl; and Y together with the carbon atoms bound thereto form an cyclobutyl, cyclopentyl, cyclohexyl, tetrahydropyranyl, tetrahydrothiopyranyl, or piperidinyl;

p is 1 to 5;

each R¹⁰ is independently selected from the group consisting of alkyl, substituted alkyl, aryl, substituted aryl, heteroaryl, substituted heteroaryl, carboxyl, carboxyl ester, and —C(O)NR⁸R⁹ where R⁸ and R⁹ are independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclic and substituted heterocyclic or, alternatively, R⁸ and R⁹, together with the nitrogen atom pendent thereto, form a heterocyclic or substituted heterocyclic ring group.

7. A compound selected from the group consisting of:

2-[(1-cyclohexyl-2-{2-fluoro-4-[3-(aminocarbonyl)-6-(4-chlorophenyl)benzyloxy]-phenyl}-1H-benzimidazole-5-carbonyl)-amino]-3-(5-hydroxy-1H-indol-3-yl)-propionic acid;

2-[(2-{4-[2-bromo-5-(4-hydroxyl-piperidine-1-carbonyl)-benzyloxy]-2-fluoro-phenyl}-1-cyclohexyl-1H-benzimidazole-5-carbonyl)-amino]-3-(5-hydroxy-1H-indol-3 -yl)-propionic acid;

2-[(1-cyclohexyl-2-{2-fluoro-4-[3-(4-hydroxyl-piperidine-1-carbonyl)-benzyloxy]-phenyl}-1H-benzimidazole-5-carbonyl)-amino]-3-(5-hydroxy-1H-indol-3-yl)-propionic acid;

2-[(2-{4-[4'-chloro 4-(4-hydroxyl-piperidine-1-carbonyl)-biphen-2-ylmethoxy]-2-fluoro-phenyl}-1-cyclohexyl-1H-benzoimidazole-5-carbonyl)-amino]-3-(5-hydroxy-1H-indol-3-yl)-propionic acid;

2-({1-Cyclohexyl-2-[4-(naphthalene-2-ylmethoxy)-phenyl]-1H-benzimidazole-5-carbonyl}-amino)-3-(5-hydroxy-1H-indol-3-yl)-propionic acid; and 3-(4-{[1-({2-[4-(4-Carbamoyl-4'-chloro-biphen-2-ylmethoxy)-2-fluoro-phenyl]-1-cyclohexyl-1H-benzoimidazole-5-carbonyl}-amino)-cyclopentanecarbonyl]-amino}-phenyl)-acrylic acid; or pharmaceutically acceptable salts thereof.

8. A pharmaceutical composition comprising a pharmaceutically acceptable diluent and a therapeutically effective amount of a compound of any one of claims 1-7 or a mixture of two or more of said compounds.

* * * * *

UNITED STATES PATENT AND TRADEMARK OFFICE
CERTIFICATE OF CORRECTION

PATENT NO. : 7,304,085 B2 Page 1 of 1
APPLICATION NO. : 10/861765
DATED : December 4, 2007
INVENTOR(S) : Roberts et al.

It is certified that error appears in the above-identified patent and that said Letters Patent is hereby corrected as shown below:

Title page,

[*] Notice: Subject to any disclaimer, the term of this patent is extended or adjusted under 35 USC 154(b) by 0 days Delete the phrase "by 0 days" and insert -- by 65 days --

Signed and Sealed this

Twenty-eighth Day of October, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aggacatgga tccgcggggt cgggcacgag acag         34

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
aaggctggca tgcactcaat gtcctacaca tggac        35